US007241941B1

(12) United States Patent
Horejsi et al.

(10) Patent No.: US 7,241,941 B1
(45) Date of Patent: Jul. 10, 2007

(54) SOYBEAN VARIETY 0137335

(75) Inventors: Thomas Horejsi, Ames, IA (US); Mark A. Erickson, Slater, IA (US); Joseph R. Byrum, West Des Moines, IA (US); Amy D. Curtis, Nevada, IA (US); Matthew J. Fox, Nevada, IA (US)

(73) Assignee: Monsanto Technology LLC, St. Louis, MO (US)

( * ) Notice: Subject to any disclaimer, the term of this patent is extended or adjusted under 35 U.S.C. 154(b) by 392 days.

(21) Appl. No.: 10/618,103

(22) Filed: Jul. 11, 2003

Related U.S. Application Data

(60) Provisional application No. 60/396,287, filed on Jul. 11, 2002.

(51) Int. Cl.
 *A01H 5/00* (2006.01)
 *A01H 5/10* (2006.01)
 *A01H 1/00* (2006.01)
 *C12N 5/04* (2006.01)

(52) U.S. Cl. ............... 800/320.1; 800/275; 800/300.1; 800/302; 435/412

(58) Field of Classification Search ............... 800/312, 800/260, 300–302; 435/415
 See application file for complete search history.

(56) References Cited

U.S. PATENT DOCUMENTS

| 5,084,082 | A |   | 1/1992  | Sebastian ............... 71/90 |
|-----------|---|---|---------|--------------------------------|
| 5,304,728 | A |   | 4/1994  | Eby ..................... 800/200 |
| 5,523,520 | A |   | 6/1996  | Hunsperger et al. ...... 800/200 |
| 5,569,815 | A |   | 10/1996 | Eby ..................... 800/200 |
| 5,576,474 | A |   | 11/1996 | Lussenden ............... 800/200 |
| 5,576,475 | A |   | 11/1996 | Matson .................. 800/200 |
| 5,650,552 | A | * | 7/1997  | Matson .................. 800/312 |
| 5,684,229 | A | * | 11/1997 | Tinius ................... 800/312 |
| 5,723,741 | A |   | 3/1998  | Matson et al. ........... 800/200 |
| 6,140,556 | A |   | 10/2000 | Conway .................. 800/312 |
| 6,162,972 | A |   | 12/2000 | Matson .................. 800/312 |
| 6,313,380 | B1|   | 11/2001 | Moots ................... 800/312 |

OTHER PUBLICATIONS

Allard, University of California, Davis, California, "Selection under self-fertilization," *Principles of Plant Breeding*, Published by John Wiley & Sons, New York, University of California, Davis, California, 50-98, 1960.
Bernard, ed., "Evaluation of Maturity Groups I and II of the U.S.D.A. Soybean Collection," pp. 1-3, 58-59, Sep. 1966.
Bernard, ed., "Evaluation of Maturity Groups III and IV of the U.S.D.A. Soybean Collection," pp. 1-3, 5a-5d, 8a-8d, 9a-9d, 14a-14d, 17a-17d, 24a-24d, and 25a-25d, Apr. 1969.
Brim and Burton, "Recurrent selection in soybeans. II. Selection for increased percent protein in seeds," *Crop Science*, 19:494-498, 1979.

Burton, J.W. 1985. Breeding soybeans for improved protein quantity and quality. p. 361-367. In R. Shibles (ed.) *Proc. 3rd World Soybean Res. Conf.*, Ames, IA. 12-17, Westview Press, Boulder, CO, 1984.
Burton, J. W. and Brim, C. A., "Recurrent selection in soybeans. III Selection for increased percent oil in seeds," *Crop Sci.*, 81: 31-34, 1981.
Byth et al., "Correlated truncated selection for yield in soybeans," *Crop Sci.*, 9:699-702, 1969.
Caldwell et al., "Selection value of phenotypic attributes in soybeans," *Crop Sci.*, 6:249-251, 1966.
Ciansio and Fehr, "Genetic variability for soybean seed composition in crosses between high and low protein parents," *J. Agric. Univ. PR*, 66:123-129, 1982.
Eshed et al., "Less-than-additive epistatic interactions of quantitative trait loci in tomato," *Genetics*, 143:1807-1817, 1996.
Fehr, "In: Soybeans: Improvement, Production and Uses," 2nd Edition, *Manograph* 16, p. 249 and 259, 1987.
Fehr, Iowa State University. "Principles of Cultivar Development," vol. 1 Theory and Technique and vol. 2 Crop Species, Soybean, Published by Macmillian Publishing Company, New York, p. 360-376, 1987.
Fulmer, "The soybean as a chemical factory," In: *Soybean Utilization Alternatives*, McCann (ed.), The Center for Alternative Crops and Products, Univ. of Minnesota, 1-12,.1988.
GRIN Database Entry PI438065 (Aug. 9, 1994), From The Internet http://www.ars-grin.gov.
GRIN Database Entry PI540555 (1988), From The Internet http://www.ars-grin.gov.
Hanson et al., "Genetic analysis of energy production in the soybean," *Crop Science*, 121-126.
Hartwig, E. E., "Breeding productive soybeans with a higher percentage of protein," In: *Seed Protein improvement in cereals and legumes*, vol. II, Intl. Atomic Energy Agency, Vienna, 59-66, 1979.
Hartwig, "Breeding soybeans for high protein content and quality," In *New approaches to breeding for improved plant protein*, International Atomic Energy Agency, Vienna, 1969.
Hartwig, E. E., "Varietal improvemen," In: *Soybeans: Improvement, production, and uses*, Caldwell (ed.), 1st edition, Agronomy, 16:187-210, 1969.
Hartwig and Hinson., "Association between chemical composition of seed and seed yield of soybeans," *Crop. Sci.*, 22:829-830, 1972.
Hymowitz, "Soybeans," In: *Evolution in crop plants*, Simmonds (ed.), Longman Group, London, 159-162, 1976.
Johnson, H. W., "Breeding for oil and protein in soybeans," *Soybean Digest*, 21(11):73-75, 1961.
Kraft et al., "Linkage disequilibrium and fingerprinting in sugar beet," *Theor. Appl. Genet.*, 101:323-326, 2000.

(Continued)

*Primary Examiner*—Elizabeth F. McElwain
(74) *Attorney, Agent, or Firm*—Fulbright & Jaworski L.L.P.

(57) ABSTRACT

The invention overcomes the deficiencies of the prior art by providing plants of soybean variety 0137335, which exhibits high seed protein and protein plus oil in combination with high yield. The invention also provides derivatives and plant parts of these plants. Further provided by the invention are methods for the use of the plant. The invention is significant in that oil and protein are important agronomic characteristics, but the value of these traits is diminished or eliminated when coupled with decreased yield.

26 Claims, No Drawings

OTHER PUBLICATIONS

Kwon and Torrie, "Heritability of and interrelationships among traits of two soybean populations," *Crop Sci.*, 4:196-198, 1964.

Leffel and Rhodes, "Agronomic performance and economic value of high-seed protein soybean," *J. Prod. Agric.*, 6:365-368, 1993.

Leffel, R. C., "High protein lines and chemical constituent pricing in soybean," *J. Prod. Agric.*, 1:111-115, 1988.

Mounts et al., "Processing and utilization," In: *Soybeans: Improvement, Production and Uses*, Wilcox (ed.), *Am. Soc. Agron.*, Madison, WI, 1987.

Nickell and Bernard, "Registration of L84-5873 and L84-5932 Soybean Germplasm Lines Resistant to Brown Stem Rot," *Crop Sci.*, 32:835, 1992.

Nickell et al., "Registration of 'Hamilton' soybean," *Crop Sci*, 30:1364, 1990.

Openshaw and Hadley, "Selection indices to modify protein concentration of soybean seeds," *Crop Sci.*, 24:1-4, 1984.

Orf, "Modifying soybean composition by plant breeding," In: *Soybean utilization alternative*, Univ. Minnesota Center Alternative Crops and Products, McCann (ed.), St. Paul, 131-141, 1988.

Pantalone et al., "Soybean fibrous root heritability and genotypic correlations with agronomic and seed quality characteristics," *Crop Sci.*, 36:1120-1125, 1996.

Sebern and Lambert, "Effect of stratification for percent protein in two soybean populations," *Crop Sci.*, 24:225-228, 1984.

Serretti et al., "Amino acid profiles of high seed protein soybean," *Crop Sci.*, 34:207-209, 1994.

Shannon et al., "Estimated gains from selection for protein and yield in the F4 generation of six soybean populations," *Crop Sci.*, 12:824-826, 1972.

Shorter et al., "Estimates of selection parameters associated with protein and oil content of soybean seeds (Glycine max (L.) Merr.)," *Aust. J. Agric. Res.*, 28:211-222, 1976.

Simpson and Wilcox, "Genetic and phenotypic associations of agronomic characteristics in four high protein soybean populations," *Crop Sci.*, 23:1077-1081, 1983.

Sneep and Hendriksen, eds., "Plant Breeding Perspectives," Wageningen: Centre for Agricultural Publishing and Documentation, 1979.

Thorne and Fehr, "Incorporation of high protein, exotic germplasm into soybean populations by 2- and 3-way crosses," *Crop Sci.*, 10:652-655, 1970.

Wehrmann et al., "Transfer of high seed protein to high-yielding soybean cultivars," *Crop Sci.*, 27:927-931, 1987.

Wilcox and Cavins, "Backcrossing high seed protein to a soybean cultivar," *Crop Sci.*, 35:1036-1041, 1995.

Wilcox, C1944 and C1945 Soybean Germplasm, *Crop Sci.*, 38(3):900, 1998.

Wilcox, C1944, Accession No. PI 599584, USDA, ARS, National Genetic Resources Program, Germplasm Resources Information Network(GRIN), 1998.

Wilcox, SN30017, Accession No. PI 599585, USDA, ARS, National Genetic Resources Program, Germplasm Resources Information Network(GRIN), 1998.

\* cited by examiner

SOYBEAN VARIETY 0137335

This application claims the priority of U.S. provisional patent application Ser. No. 60/396,287, filed Jul. 11, 2002, the entire disclosure of which is incorporated herein by reference.

BACKGROUND OF THE INVENTION

1. Field of the Invention

The present invention relates generally to the field of soybean breeding. In particular, the invention relates to soybean variety 0137335.

2. Description of Related Art

The soybean is an excellent source of protein (Mounts et al., 1987; Fulmer, 1988) and has the potential to supply adequate and nutritious food and feed for use by ever-increasing world production. Current soybean cultivars average approximately 41% protein and 21% oil in the seed on a dry weight basis (Leffel and Rhodes, 1993).

Most commercially produced soybeans are processed to produce edible oil and one or more protein products. The initial protein fraction is a soybean meal, either containing the fiber from the seed hull (44% protein soymeal) or separated from the hull fiber (48.5% protein soymeal). The initial meal fraction is often further processed to produce more highly refined protein products, primarily soy protein concentrate or soy protein isolate. In any of these protein fractions—meal, concentrate or isolate—the protein component is of economic or nutritional value. Soy protein is valued for its high nutritional quality for people and livestock, and for functional properties, such as gel and foam formation. Alternative processing methods produce protein-based soy foods, such as tofu or soymilk. With the economic value of soy protein, soybeans with higher concentration of protein are very desirable. However, higher protein content cannot be associated with lower oil content or lower seed yield per acre if an economic benefit is to be obtained.

Breeding programs for increased protein content of soybean seed have been in progress for many years (Burton, J. W. 1985; Hartwig, E. E. 1969; Hartwig, E. E. 1979; Johnson, H. W. 1961; and Leffel, R. C. 1988). However, with a few exceptions, high protein soybeans developed to date have not been as high in yield as commercial cultivars. Studies have shown negative genetic correlations between soybean seed yield and protein content (Caldwell et al., 1966; Hinson et al. 1972; Kwon and Torrie, 1964; Thorne and Fehr, 1970; Burton, 1988; Leffel and Rhodes, 1993; Serretti et al., 1994; Pantalone et al., 1996; Simpson and Wilcox, 1983: Shannon et al. 1972). The high negative correlation between the traits lead Hartwig (1973) to conclude that it is not possible to retain high oil along with high protein content. Openshaw and Hadley (1984) concluded that breeding methods designed to increase both protein and oil showed limited success. Orf (1988) concluded that producing soybean varieties with high protein, high oil, and high yield will be difficult from a breeding standpoint and may not be a realistic conventional breeding objective. Hymowitz (1976) indicated that it is probable that lower protein soybeans will be caused in the long term if an emphasis is maintained on the yield of soybeans.

The negative association has a strong genetic basis (tight linkages, pleiotropy, or both), and selection for percent protein should result in reduced yield. Studies of selection indices involving both yield and percent protein have generally confirmed the negative relationship. Caldwell et al. (1966) predicted a yield decrease when percent protein was the sole selection criterion. Burton (1984) summarized the results of several breeding studies, reporting genotypic correlations between seed yield and seed protein percentage varying from −0.12 to −0.74. In only one population was there a positive genotypic correlation between these two traits. Additional studies by Sebern and Lambert (1984), Simpson and Wilcox (1983), and Wehrmann et al. (1987) reported moderate to strong inverse relationships between seed yield and seed protein with correlation coefficients ranging from −0.23 to −0.86.

In the past, the pedigree and backcrossing methods have been used with limited success to select soybean lines with high percent protein. Cianzio and Fehr (1982) evaluated seed protein and oil of $F_2$-derived lines in the $F_2$ generation and $BC_1F_1$-derived and $BC_2F_1$-derived lines in the $F_3$ generation of crosses between the high protein lines Pando and PI 153.269 and the high yielding cultivars Wells and Woodworth. No line from either set of crosses had protein concentration as high as those of the high protein donor parent. Mean protein percentages and genetic variances of the populations decreased with each backcross to the high yielding parent. The results indicated to them that it will be difficult to transfer genes for extremely high protein levels to cultivars with lower protein. No yield data were recorded on the breeding lines evaluated in this study.

Wehrmann et al.(1987) evaluated 95 $BC_2$ progenies in each of three populations, where the recurrent parents were high yielding lines and the donor parent was Pando, that averaged 480 g kg$^{-1}$ seed protein. In these populations, no backcross-derived lines were recovered that combined exceptionally high seed protein with the yield of the recurrent parent. In each of two populations, the highest protein line averaged only 422 and 433 g kg$^{-1}$ protein and did not differ significantly in yield or seed oil from the recurrent parent. In the third population, the highest protein line averaged 462 g kg$^{-1}$ protein but was significantly lower in both yield and seed oil concentration than the recurrent parent.

There have been isolated reports that genotypic correlations between seed yield and seed protein percentage may not be as strong as the literature has indicated (Byth et al. 1969; Wilcox and Cavins, 1995). However, none of the backcross studies evaluated progenies beyond the $BC_3$ generation. The lack of success in transferring exceptionally high seed protein to high yielding cultivars by backcrossing has cast doubt on the possibility of combining these two traits in adapted germplasm or cultivars.

All crop species are grown for the purpose of harvesting some product of commercial significance. Enhancement of productivity or yield of that product is a major goal of most plant breeding programs. The highest priority in most soybean cultivar development programs is increasing seed yield. Seed yield is a quantitative character controlled by many genes and strongly influenced by the environment. The heritability of yield is the lowest and the most variable of the major agronomic traits considered in cultivar development, with heritability estimates ranging from 3 to 58%. Yield is an example of a quantitative character that breeders attempt to improve beyond the level of that present in current cultivars. Disease resistance is required in most cases to protect the yield potential of a cultivar.

It is a difficult challenge to incorporate increased protein or oil content into high yielding cultivars given the negative correlations observed among the traits. The difficulty of obtaining a commercially acceptable variety is increased several fold if a breeder attempts to significantly increase total protein without a loss in oil content into one cultivar.

Perhaps because of these difficulties, the prior art has failed to provide high yielding soybean varieties that posses high seed protein without decreased seed oil. However, there is a great need in the art for such soybean plants. Increased seed protein can significantly improve the value of a soybean harvest. For the increase in seed protein to have commercial significance, yield and/or oil content must not be substantially impacted. Therefore, providing soybean plants that are both high yielding and posses high combined protein and oil would represent a substantial advance in the art and benefit farmers and consumers alike.

SUMMARY OF THE INVENTION

In one aspect, the invention provides an agronomically elite soybean plant of variety 0137335. Also provided are the parts of this plant, including, but not limited to, pollen, an ovule, a cell and a seed. Further provided is a tissue culture of regenerable cells of the plant, wherein the tissue culture regenerates soybean plants capable of expressing all the physiological and morphological characteristics of the plant. In one embodiment of the invention, the regenerable cells are embryos, meristematic cells, pollen, leaves, roots, root tips or flowers or are protoplasts or callus derived therefrom. Further provided by the invention is a soybean plant regenerated from the tissue culture and capable of expressing all the physiological and morphological characteristics of the plants of the invention.

A plant of the invention may, in certain embodiments, further comprise a single locus conversion. Examples of such a single locus conversion include, but are not limited to, a dominant allele, a recessive allele, s single locus stably inserted into a soybean genome by transformation and a single gene.

In yet another aspect, the invention provides method of producing soybean seed, comprising crossing a plant of the invention with itself or a second soybean plant. In certain embodiments of the invention, the method may be further defined as a method of preparing hybrid soybean seed, comprising crossing the plant to a second, distinct soybean plant. In one embodiment of the invention, the crossing comprises the steps of: (a) planting a seed of a starting plant of the invention and a second, distinct soybean plant; (b) growing soybean plants from the seed until the plants bear flowers; (c) cross pollinating a flower of the starting plant with pollen from the second soybean plant or cross pollinating a flower of the second soybean plant with pollen from the starting plant; and (d) harvesting seed resulting from the cross pollinating.

In still yet another aspect, the invention provides a method for developing a soybean plant in a soybean breeding program comprising: (a) obtaining a soybean plant, or its parts, provided by the invention; and (b) employing the plant or parts as a source of breeding material using plant breeding techniques. In one embodiment of the invention, the plant breeding techniques may be selected from the group consisting of recurrent selection, mass selection, bulk selection, backcrossing, pedigree breeding, genetic marker-assisted selection and genetic transformation. In the method, the plant of the invention may be used as a male or female parent In still yet another aspect, the invention provides a method of producing a soybean plant derived from a starting plant of the invention, the method comprising the steps of: (a) preparing a progeny plant derived from the starting plant by crossing a plant of the plant with a second soybean plant; and (b) crossing the progeny plant with itself or a second plant to produce a progeny plant of a subsequent generation which is derived from the starting plant. In one embodiment of the invention, the method may further comprise: (c) crossing the progeny plant of a subsequent generation with itself or a second plant; and (d) repeating steps (b) and (c) for at least 2–10 additional generations to produce an soybean plant derived from the starting plant. In certain embodiments of the invention, the method may be further defined as a method of producing a soybean plant with increased seed protein plus oil content, wherein the soybean plant comprises increased seed protein plus oil content relative to the second soybean plant; may be further defined as a method of producing a soybean plant with increased protein content, wherein the soybean plant comprises increased seed protein content relative to the second soybean plant; and may be further defined as a method of producing a soybean plant with increased seed oil and protein plus oil content, wherein the soybean plant comprises increased seed protein and protein plus oil content relative to the second soybean plant. The method may additionally further comprise: (a) crossing the plant derived from the starting plant of the invention with itself or another soybean plant to yield seed of additional progeny derived from the starting plant; (b) growing the seed under plant growth conditions to yield additional plants derived from the starting plant; and (c) repeating the crossing and growing steps of (a) and (b) from 0 to 7 times to generate further plants derived from the starting plant. Still further provided are plants or parts thereof produced by this method.

DETAILED DESCRIPTION OF THE INVENTION

The invention overcomes the deficiencies of the prior art by providing soybean varieties that express a commercially significant yield and high seed protein without decreased seed oil content (e.g., high protein plus oil). In particular, the invention provides, for the first time, plants of high yielding agronomically elite soybean varieties with a mean whole seed total protein content of greater than 44% and a mean whole seed total protein plus oil content of greater than 64%. Such agronomically elite plants may have, for example, a commercially significant yield. The prior art has failed to provide plants of such a variety, presumably because of the negative correlation observed between these traits (Hartwig, 1973). While plants of a variety with one and, in some instances, two of the high protein, protein plus oil or yield traits have been prepared, these traits have not been successfully combined. By describing the production of such plants and providing these plants, the invention now allows the preparation of a potentially unlimited number of novel soybean varieties exhibiting a commercially significant yield with combined high seed protein and protein plus oil. This is because, once such an elite variety is produced and/or parent plants for the production of the variety are identified, then the combined protein and oil attribute can be transferred to other varieties with appropriate backcross and selection to maintain the desirable traits, as is described herein below.

There are numerous steps in the development of any novel, desirable plant germplasm, such as the lines described herein or varieties derived therefrom using the methods of the invention. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. In addition to a commercially significant yield and high protein plus oil, these important traits may include, for example, resistance to diseases and insects, better stems and roots, tolerance to drought and heat, better agronomic quality, resistance to herbicides, and improvements in various compositional traits.

Choice of breeding or selection methods depends on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, recurrent selection and backcrossing. Methods that may be employed in connection with the instant invention are described in detail herein below.

I. PLANTS OF THE INVENTION

The invention provides plants and derivatives thereof of soybean varieties that combine commercially significant yield and high protein without a corresponding reduction in seed oil. In particular, the invention provides, for the first time, plants and derivatives of high yielding agronomically elite soybean varieties with a mean whole seed total protein content of greater than 44% and a mean whole seed total protein plus oil content of greater than 64%. Such agronomically elite plants may have, for example, a yield in excess of 35 bushels per acre. In certain embodiments of the invention, the mean seed oil content of the plants of the invention may be greater than 44%, 45%, 46%, 48%, or 50%. The plants of the invention may further comprise a mean whole seed total protein plus oil content of greater than 64%, 66%, 68%, or 70%. In one embodiment of the invention, the mean whole seed total protein content is at least 45% and up to 50%, and the mean whole seed total protein plus oil content is greater than 66% and up to about 70%. In further embodiments of the invention, the mean whole seed total protein content at least 46% and up to 50%, and the mean whole seed total protein plus oil content is greater than 68% and up to about 70%.

As described herein above, a major advance of the invention is that the plants of the invention are of varieties providing high protein plus oil and a commercially significant yield. As used herein, a commercially significant yield is defined as a mean yield of at least 35 bushels per acre, such as at least 36, 37, 38, 40, 42, 44 or more bushels per acre, including from at least 35 bushels per acre to about 50, about 55 and about 60 or more bushels per acre.

Examples of soybean plant varieties provided by the invention and exhibiting a commercially significant yield in combination with high seed protein and protein plus oil are the soybean varieties 0007583, 0008079, 0137335, 0137472, 0137441 and 0137810. One aspect of the current invention is thus directed to plants and parts thereof of these varieties and methods for using these plants and plant parts. Plant parts of these varieties include, but are not limited to, pollen, an ovule and a cell. Still further, the invention provides tissue cultures of regenerable cells of these varieties, which cultures regenerate soybean plants capable of expressing all the physiological and morphological characteristics of the variety. Such regenerable cells may include embryos, meristematic cells, pollen, leaves, roots, root tips or flowers, or protoplasts or callus derived therefrom. Also provided by the invention are soybean plants regenerated from such a tissue culture, wherein the plants are capable of expressing all the physiological and morphological characteristics of the plant variety from which the regenerable cells were obtained. A plant of these varieties may further comprise a single locus conversion. Examples of such single locus conversions include a dominant allele, a recessive allele, a single locus stably inserted into a soybean genome by transformation and a single locus comprising a single gene.

The current invention also provides methods of crossing the soybean plants of the invention. In one embodiment, the plant of the invention is of soybean variety 0007583, 0008079, 0137335, 0137472, 0137441 or 0137810. The method may comprise crossing the plant with itself or a second soybean plant. Where the plant is crossed with a second, distinct plant, a hybrid is produced. Crossing may comprise, for example, planting a seed of a variety and a second, distinct soybean plant; growing soybean plants from the seed until the plants bear flowers; cross pollinating a flower of the first plant with pollen from the second soybean plant or cross pollinating a flower of the second soybean plant with pollen from the first plant; and harvesting seed resulting from the cross pollinating.

Further provided by the invention is a method for developing a soybean plant in a soybean breeding program comprising: obtaining a soybean plant of the invention, or its parts, and employing the plant or parts as a source of breeding material using plant breeding techniques. Such a variety may, in certain embodiments of the invention, include the soybean varieties 0007583, 0008079, 0137335, 0137472, 0137441 or 0137810. Plant breeding techniques that can be used in the method include recurrent selection, mass selection, bulk selection, backcrossing, pedigree breeding, genetic marker-assisted selection and genetic transformation. In the technique, the soybean plant of the invention can be used as a male or female parent.

Further provided by the invention are methods of producing a soybean plant of a variety derived from a plant of the invention comprising the steps of: (a) preparing a progeny plant derived from a plant of the invention by crossing the plant with a second soybean plant; and (b) crossing the progeny plant with itself or a second plant to produce a progeny plant of a subsequent generation which is derived from a plant of the invention. The method may further comprise: (c) crossing the progeny plant of a subsequent generation with itself or a second plant; and (d) repeating steps (b) and (c) for at least 2–10 additional generations to produce an soybean plant derived from a plant of the invention. Such a method may, in certain embodiments of the invention, be further defined as a method of producing a soybean plant with increased seed protein and/or protein plus oil content, wherein the soybean plant of the invention and the progeny plant comprise increased seed protein and/or protein plus oil relative to the second soybean plant. The invention further provides plants produced by this method. The method may still further comprise (a) crossing the plant derived from the plant of the invention with itself or another soybean plant to yield additional progeny derived from derived from a plant of the invention; (b) growing the progeny soybean seed of step (a) under plant growth conditions, to yield additional plants derived from the plant of the invention; (c) repeating the crossing and growing steps of (a) and (b) from 0 to 7 times to generate further plants derived from derived from the plant of the invention. The invention also provides plants produced by this method.

II. BREEDING THE PLANTS OF THE INVENTION

The plants of the invention may be used in breeding protocols for the development of new plants and plant varieties. One aspect of the current invention thus concerns methods for crossing a soybean plant of the invention with itself or a second plant and the seeds and plants produced by such methods. These methods can be used for propagation of a soybean variety, or can be used to produce hybrid soybean seeds and the plants grown therefrom. Hybrid soybean plants can be used for commercial production of soy products or may be advanced in breeding protocols for the production of novel soybean varieties. The varieties provided by the present invention are well suited to the development of new varieties based on the elite nature of the genetic background of the varieties, and particularly the high protein and protein plus oil content of the varieties in combination with high yield. A hybrid plant can also be used as a recurrent parent at any given stage in a backcrossing protocol during the production of a single locus conversion of a given soybean variety.

In selecting a second plant to cross with a plant of the invention for the purpose of developing novel soybean varieties, it will typically be desired to choose those plants which themselves exhibit one or more selected desirable characteristics. Examples of potentially desired characteristics include seed yield, lodging resistance, emergence, seedling vigor, disease tolerance, maturity, plant height, high protein content, high protein plus oil and shattering resistance.

The complexity of inheritance influences the choice of breeding method. Backcross breeding is used to transfer one or a few favorable genes for a highly heritable trait into a desirable variety. This approach has been used extensively for breeding disease-resistant varieties (Bowers et al., 1992; Nickell and Bernard, 1992). Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful varieties produced per unit of input (e.g., per year, per dollar expended, etc.).

Promising advanced breeding lines are thoroughly tested and compared to appropriate standards in environments representative of the commercial target area(s) for generally three or more years. The best lines are candidates for new commercial varieties. Those still deficient in a few traits may be used as parents to produce new populations for further selection.

These processes, which lead to the final step of marketing and distribution, may take as much as eight to 12 years from the time the first cross is made. Therefore, development of new varieties is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to one or more widely grown standard varieties. Single observations are generally inconclusive, while replicated observations provide a better estimate of genetic worth.

The goal of plant breeding is to develop new, unique and superior soybean varieties and hybrids. The breeder initially selects and crosses two or more parental lines, followed by repeated selfing and selection, producing many new genetic combinations. Each year, the plant breeder selects the germplasm to advance to the next generation. This germplasm is grown under unique and different geographical, climatic and soil conditions, and further selections are then made, during and at the end of the growing season. The varieties which are developed can be unpredictable. This unpredictability is because the breeder's selection occurs in unique environments, generally with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same variety twice by using the exact same original parents and the same selection techniques. This unpredictability results in the expenditure of large amounts of research monies to develop superior new soybean varieties. However, by identification of starting germplasm sources, certain traits can be passed on to progeny by way of a series of selections and crosses. While any given progeny resulting from a given parent cross cannot be predicted to have a certain trait, selection of progeny with a desired trait or combination of traits of one or both parents can be repeatedly made though observation and selection of progeny at various generations. Once starting parent lines have been identified possessing one or more desired traits, further progeny can be prepared having the desired traits through routine and repeated crosses and selections.

The development of new soybean varieties requires the development and selection of soybean varieties, the crossing of these varieties and selection of progeny from the superior hybrid crosses. The hybrid seed is produced by manual crosses between selected male-fertile parents or by using male sterility systems. Hybrids may be identified by using certain single locus traits such as pod color, flower color, pubescence color or herbicide resistance which indicate that the seed is truly a hybrid. Additional data on parental lines as well as the phenotype of the hybrid influence the breeder's decision whether to continue with the specific hybrid cross.

Pedigree breeding and recurrent selection breeding methods are used to develop varieties from breeding populations. Breeding programs combine desirable traits from two or more varieties or various broad-based sources into breeding pools from which varieties are developed by selfing and selection of desired phenotypes. The new varieties are evaluated to determine which have commercial potential.

Pedigree breeding is commonly used for the improvement of self-pollinating crops. Two parents which possess favorable, complementary traits are crossed to produce an $F_1$. An $F_2$ population is produced by selfing one or several $F_1$'s. Selection of the best individuals may begin in the $F_2$ population (or later depending upon the breeders objectives); then, beginning in the $F_3$, the best individuals in the best families can be selected. Replicated testing of families can begin in the $F_3$ or $F_4$ generation to improve the effectiveness of selection for traits with low heritability. At an advanced stage of inbreeding (i.e., $F_6$ and $F_7$), the best lines or mixtures of phenotypically similar lines are tested for potential release as new varieties.

Mass and recurrent selections can be used to improve populations of either self-or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genetic loci for simply inherited, highly heritable traits into a desirable homozygous variety which is the recurrent parent. The source of the trait to be transferred is called the donor or nonrecurrent parent. The resulting plant is expected to have the attributes of the recurrent parent (e.g., variety) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., variety) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, 1960; Simmonds, 1979; Sneep et al., 1979; Fehr, 1987a,b).

Proper testing should detect any major faults and establish the level of superiority or improvement over current varieties. In addition to showing superior performance, there must be a demand for a new variety that is compatible with industry standards or which creates a new market. The introduction of a new variety will incur additional costs to the seed producer, the grower, processor and consumer; for special advertising and marketing, altered seed and commercial production practices, and new product utilization. The testing preceding release of a new variety should take into consideration research and development costs as well as technical superiority of the final variety. For seed-propagated varieties, it must be feasible to produce seed easily and economically.

Soybean, *Glycine max* (L), is an important and valuable field crop. Thus, a continuing goal of plant breeders is to develop stable, high yielding soybean varieties that are agronomically sound. The reasons for this goal are to maximize the amount of grain produced on the land used and to supply food for both animals and humans. To accomplish this goal, the soybean breeder must select and develop soybean plants that have the traits that result in superior varieties.

The effectiveness of selecting for genotypes with traits of interest (e.g., high yield, disease resistance, protein and/or protein plus oil attributes) in a breeding program will depend upon: 1) the extent to which the variability in the traits of interest of individual plants in a population is the result of genetic factors and is thus transmitted to the progenies of the selected genotypes; and 2) how much the variability in the traits of interest (yield, disease traits, protein and/or protein plus oil attributes) among the plants is due to the environment in which the different genotypes are growing. The inheritance of traits ranges from control by one major gene whose expression is not influenced by the environment (i.e., qualitative characters) to control by many genes whose effects are greatly influenced by the environment (i.e., quantitative characters). Breeding for quantitative traits is further characterized by the fact that: 1) the differences resulting from the effect of each gene are small, making it difficult or impossible to identify them individually; 2) the number of genes contributing to a character is large, so that distinct segregation ratios are seldom if ever obtained; and 3) the effects of the genes may be expressed in different ways based on environmental variation. Therefore, the accurate identification of transgressive segregates or superior genotypes with the traits of interest is extremely difficult and its success is dependent on the plant breeder's ability to minimize the environmental variation affecting the expression of the quantitative character in the population. The likelihood of identifying a transgressive segregant is greatly reduced as the number of traits combined into one genotype is increased. For example, if a cross is made between cultivars differing in three complex characters, such as yield, disease resistance and protein and/or protein plus oil attributes, it is extremely difficult to recover simultaneously by recombination the maximum number of favorable genes for each of the three characters into one genotype. Consequently, all the breeder can generally hope for is to obtain a favorable assortment of genes for the first complex character combined with a favorable assortment of genes for the second character into one genotype in addition to a herbicide resistant gene.

The methods used in cultivar development programs and their probability of success are dependent on the number of characters to be improved simultaneously, such as, seed yield, disease resistance, and protein and/or protein plus oil attributes. The proportion of desired individuals for multiple characters in a population is obtained by multiplying together the proportion of desired individuals expected in the population for each character to be improved. This assumes that the characters are inherited independently, i.e., are not genetically linked.

These principles can be applied not only to traditionally bred lines, but to transgenic lines as well. Whether combining desirable traditional and transgenic traits via hybridization of transgenic lines or co-transformation of multiple genes into one line, the combined effect on yield are likely to be multiplicative. For example, if the probability that suitable yields and disease resistance are found in 1% of lines transformed with a highly heritable attribute then the probability that combining three such attributes ought to be 0.01×0.01×0.01 or 1×10−6.

Soybean plants (*Glycine max* L.) can be crossed by either natural or mechanical techniques (see, e.g., Fehr, 1980). Natural pollination occurs in soybeans either by self pollination or natural cross pollination, which typically is aided by pollinating organisms. In either natural or artificial crosses, flowering and flowering time are an important consideration. Soybean is a short-day plant, but there is considerable genetic variation for sensitivity to photoperiod (Hamner, 1969; Criswell and Hume, 1972). The critical day length for flowering ranges from about 13 h for genotypes adapted to tropical latitudes to 24 h for photoperiod-insensitive genotypes grown at higher latitudes (Shibles et al., 1975). Soybeans seem to be insensitive to day length for 9 days after emergence. Photoperiods shorter than the critical day length are required for 7 to 26 days to complete flower induction (Borthwick and Parker, 1938; Shanmugasundaram and Tsou, 1978).

Sensitivity to day length is an important consideration when genotypes are grown outside of their area of adaptation. When genotypes adapted to tropical latitudes are grown in the field at higher latitudes, they may not mature before frost occurs. Plants can be induced to flower and mature earlier by creating artificially short days or by grafting (Fehr, 1980). Soybeans frequently are grown in winter nurseries located at sea level in tropical latitudes where day lengths are much shorter than their critical photoperiod. The short day lengths and warm temperatures encourage early flowering and seed maturation, and genotypes can produce a seed crop in 90 days or fewer after planting. Early flowering is useful for generation advance when only a few self-pollinated seeds per plant are needed, but not for artificial hybridization because the flowers self-pollinate before they are large enough to manipulate for hybridization. Artificial lighting can be used to extend the natural day length to about 14.5 h to obtain flowers suitable for hybridization and to increase yields of self-pollinated seed.

The effect of a short photoperiod on flowering and seed yield can be partly offset by altitude, probably due to the effects of cool temperature (Major et al., 1975). At tropical latitudes, varieties adapted to the northern U.S. perform more like those adapted to the southern U.S. at high altitudes than they do at sea level.

The light level required to delay flowering is dependent on the quality of light emitted from the source and the genotype being grown. Blue light with a wavelength of about 480 nm requires more than 30 times the energy to inhibit flowering as red light with a wavelength of about 640 nm (Parker et al., 1946).

Temperature can also play a significant role in the flowering and development of soybean (Major et al., 1975). It can influence the time of flowering and suitability of flowers for hybridization. Temperatures below 21° C. or above 32° C. can reduce floral initiation or seed set (Hamner, 1969; van Schaik and Probst, 1958). Artificial hybridization is most successful between 26° C. and 32° C. because cooler temperatures reduce pollen shed and result in flowers that self-pollinate before they are large enough to manipulate. Warmer temperatures frequently are associated with increased flower abortion caused by moisture stress; however, successful crosses are possible at about 35° C. if soil moisture is adequate.

Soybeans have been classified as indeterminate, semi-determinate, and determinate based on the abruptness of stem termination after flowering begins (Bernard and Weiss, 1973). When grown at their latitude of adaptation, indeterminate genotypes flower when about one-half of the nodes on the main stem have developed. They have short racemes with few flowers, and their terminal node has only a few flowers. Semi-determinate genotypes also flower when about one-half of the nodes on the main stem have developed, but node development and flowering on the main stem stops more abruptly than on indeterminates. Their racemes are short and have few flowers, except for the terminal one, which may have several times more flowers than those lower on the plant. Determinate varieties begin flowering when all or most of the nodes on the main stem have developed. They usually have elongated racemes that may be several centimeters in length and may have a large number of flowers. Stem termination and flowering habit are reported to be controlled by two major genes (Bernard and Weiss, 1973).

Soybean flowers typically are self-pollinated on the day the corolla opens. The amount of natural crossing, which is typically associated with insect vectors such as honeybees, is approximately 1% for adjacent plants within a row and 0.5% between plants in adjacent rows. The structure of soybean flowers is similar to that of other legume species and consists of a calyx with five sepals, a corolla with five petals, 10 stamens, and a pistil (Carlson, 1973). The calyx encloses the corolla until the day before anthesis. The corolla emerges and unfolds to expose a standard, two wing petals, and two keel petals. An open flower is about 7 mm long from the base of the calyx to the tip of the standard and 6 mm wide across the standard. The pistil consists of a single ovary that contains one to five ovules, a style that curves toward the standard, and a club-shaped stigma. The stigma is receptive to pollen about 1 day before anthesis and remains receptive for 2 days after anthesis, if the flower petals are not removed. Filaments of nine stamens are fused, and the one nearest the standard is free. The stamens form a ring below the stigma until about 1 day before anthesis, then their filaments begin to elongate rapidly and elevate the anthers around the stigma. The anthers dehisce on the day of anthesis, pollen grains fall on the stigma, and within 10 h the pollen tubes reach the ovary and fertilization is completed (Johnson and Bernard, 1963).

Self-pollination occurs naturally in soybean with no manipulation of the flowers. For the crossing of two soybean plants, it is typically preferable, although not required, to utilize artificial hybridization. In artificial hybridization, the flower used as a female in a cross is manually cross pollinated prior to maturation of pollen from the flower, thereby preventing self fertilization, or alternatively, the male parts of the flower are emasculated using a technique known in the art. Techniques for emasculating the male parts of a soybean flower include, for example, physical removal of the male parts, use of a genetic factor conferring male sterility, and application of a chemical gametocide to the male parts.

For artificial hybridization employing emasculation, flowers that are expected to open the following day are selected on the female parent. The buds are swollen and the corolla is just visible through the calyx or has begun to emerge. Usually no more than two buds on a parent plant are prepared, and all self-pollinated flowers or immature buds are removed with forceps. Special care is required to remove immature buds that are hidden under the stipules at the leaf axil, and could develop into flowers at a later date. The flower is grasped between the thumb and index finger and the location of the stigma determined by examining the sepals. A long, curvy sepal covers the keel, and the stigma is on the opposite side of the flower. The calyx is removed by grasping a sepal with the forceps, pulling it down and around the flower, and repeating the procedure until the five sepals are removed. The exposed corolla is removed by grasping it just above the calyx scar, then lifting and wiggling the forceps simultaneously. Care is taken to grasp the corolla low enough to remove the keel petals without injuring the stigma. The ring of anthers is visible after the corolla is removed, unless the anthers were removed with the petals. Cross-pollination can then be carried out using, for example, petri dishes or envelopes in which male flowers have been collected. Desiccators containing calcium chloride crystals are used in some environments to dry male flowers to obtain adequate pollen shed.

It has been demonstrated that emasculation is unnecessary to prevent self-pollination (Walker et al., 1979). When emasculation is not used, the anthers near the stigma frequently are removed to make it clearly visible for pollination. The female flower usually is hand-pollinated immediately after it is prepared; although a delay of several hours does not seem to reduce seed set. Pollen shed typically begins in the morning and may end when temperatures are above 30° C., or may begin later and continue throughout much of the day with more moderate temperatures.

Pollen is available from a flower with a recently opened corolla, but the degree of corolla opening associated with pollen shed may vary during the day. In many environments, it is possible to collect male flowers and use them immediately without storage. In the southern U.S. and other humid climates, pollen shed occurs in the morning when female flowers are more immature and difficult to manipulate than in the afternoon, and the flowers may be damp from heavy dew. In those circumstances, male flowers are collected into envelopes or petri dishes in the morning and the open container is typically placed in a desiccator for about 4 h at a temperature of about 25° C. The desiccator may be taken to the field in the afternoon and kept in the shade to prevent excessive temperatures from developing within it. Pollen viability can be maintained in flowers for up to 2 days when stored at about 5° C. In a desiccator at 3° C., flowers can be stored successfully for several weeks; however, varieties may differ in the percentage of pollen that germinates after long-term storage (Kuehl, 1961).

Either with or without emasculation of the female flower, hand pollination can be carried out by removing the stamens and pistil with a forceps from a flower of the male parent and gently brushing the anthers against the stigma of the female flower. Access to the stamens can be achieved by removing the front sepal and keel petals, or piercing the keel with closed forceps and allowing them to open to push the petals away. Brushing the anthers on the stigma causes them to rupture, and the highest percentage of successful crosses is obtained when pollen is clearly visible on the stigma. Pollen shed can be checked by tapping the anthers before brushing the stigma. Several male flowers may have to be used to obtain suitable pollen shed when conditions are unfavorable, or the same male may be used to pollinate several flowers with good pollen shed.

When male flowers do not have to be collected and dried in a desiccator, it may be desired to plant the parents of a cross adjacent to each other. Plants usually are grown in rows 65 to 100 cm apart to facilitate movement of personnel within the field nursery. Yield of self-pollinated seed from an individual plant may range from a few seeds to more than 1,000 as a function of plant density. A density of 30 plants/m of row can be used when 30 or fewer seeds per plant is adequate, 10 plants/m can be used to obtain about 100 seeds/plant, and 3 plants/m usually results in maximum seed production per plant. Densities of 12 plants/m or less commonly are used for artificial hybridization.

Multiple planting dates about 7 to 14 days apart usually are used to match parents of different flowering dates. When differences in flowering dates are extreme between parents, flowering of the later parent can be hastened by creating an artificially short day or flowering of the earlier parent can be delayed by use of artificially long days or delayed planting. For example, crosses with genotypes adapted to the southern U.S. are made in northern U.S. locations by covering the late genotype with a box, large can, or similar container to create an artificially short photoperiod of about 12 h for about 15 days beginning when there are three nodes with trifoliate leaves on the main stem. Plants induced to flower early tend to have flowers that self-pollinate when they are small and can be difficult to prepare for hybridization.

Grafting can be used to hasten the flowering of late flowering genotypes. A scion from a late genotype grafted on a stock that has begun to flower will begin to bloom up to 42 days earlier than normal (Kiihl et al., 1977). First flowers on the scion appear from 21 to 50 days after the graft.

Genetic male sterility is available in soybeans and may be useful to facilitate hybridization in the context of the current invention, particularly for recurrent selection programs (Brim and Stuber, 1973). The distance required for complete isolation of a crossing block is not clear; however, outcrossing is less than 0.5% when male-sterile plants are 12 m or more from a foreign pollen source (Boerma and Moradshahi, 1975). Plants on the boundaries of a crossing block probably sustain the most outcrossing with foreign pollen and can be eliminated at harvest to minimize contamination.

Cross-pollination is more common within rows than between adjacent rows; therefore, it may be preferable to grow populations with genetic male sterility on a square grid to create rows in all directions. For example, single-plant hills on 50-cm centers may be used, with subdivision of the area into blocks of an equal number of hills for harvest from bulks of an equal amount of seed from male-sterile plants in each block to enhance random pollination.

Observing pod development 7 days after pollination generally is adequate to identify a successful cross. Abortion of pods and seeds can occur several weeks after pollination, but the percentage of abortion usually is low if plant stress is minimized (Shibles et al., 1975). Pods that develop from artificial hybridization can be distinguished from self-pollinated pods by the presence of the calyx scar, caused by removal of the sepals. The sepals begin to fall off as the pods mature; therefore, harvest should be completed at or immediately before the time the pods reach their mature color. Harvesting pods early also avoids any loss by shattering.

Once harvested, pods are typically air-dried at not more than 38° C. until the seeds contain 13% moisture or less, then the seeds are removed by hand. Seed can be stored satisfactorily at about 25° C. for up to a year if relative humidity is 50% or less. In humid climates, germination percentage declines rapidly unless the seed is dried to 7% moisture and stored in an air-tight container at room temperature. Long-term storage in any climate is best accomplished by drying seed to 7% moisture and storing it at 10° C. or less in a room maintained at 50% relative humidity or in an air-tight container.

III. SINGLE LOCUS CONVERSIONS

When the term soybean variety is used in the context of the present invention, this also includes any single locus conversions of that variety. The term single locus converted plant as used herein refers to those soybean plants which are developed by a plant breeding technique called backcrossing, wherein essentially all of the desired morphological and physiological characteristics of a variety are recovered in addition to the single locus transferred into the variety via the backcrossing technique. Backcrossing methods can be used with the present invention to improve or introduce a characteristic into the present variety. The term backcrossing as used herein refers to the repeated crossing of a hybrid progeny back to one of the parental soybean plants for that hybrid. The parental soybean plant which contributes the locus for the desired characteristic is termed the nonrecurrent or donor parent. This terminology refers to the fact that the nonrecurrent parent is used one time in the backcross protocol and therefore does not recur. The parental soybean plant to which the locus or loci from the nonrecurrent parent are transferred is known as the recurrent parent as it is used for several rounds in the backcrossing protocol (Poehlman et al., 1995; Fehr, 1987a,b; Sprague and Dudley, 1988).

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a soybean plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Soybean varieties can also be developed from more than two parents (Fehr, 1987a). The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, enhanced nutritional quality, yield stability, and yield enhancement. These comprise genes generally inherited through the nucleus.

Direct selection may be applied where the single locus acts as a dominant trait. An example of a dominant trait is the herbicide resistance trait. For this selection process, the progeny of the initial cross are sprayed with the herbicide prior to the backcrossing. The spraying eliminates any plants which do not have the desired herbicide resistance characteristic, and only those plants which have the herbicide resistance gene are used in the subsequent backcross. This process is then repeated for all additional backcross generations.

One type of single locus trait having particular utility is a gene which confers resistance to the herbicide glyphosate. Glyphosate inhibits the action of the enzyme EPSPS, which is active in the biosynthetic pathway of aromatic amino acids. Inhibition of this enzyme leads to starvation for the amino acids phenylalanine, tyrosine, and tryptophan and secondary metabolites derived therefrom. Mutants of this enzyme are available which are resistant to glyphosate. For example, U.S. Pat. No. 4,535,060 describes the isolation of EPSPS mutations which confer glyphosate resistance upon organisms having the *Salmonella typhimurium* gene for EPSPS, termed aroA. A mutant EPSPS gene having similar mutations also has been cloned from *Zea mays*. The mutant gene encodes a protein with amino acid changes at residues 102 and 106. When these or other similar genes are introduced into a plant by genetic transformation, a herbicide resistant phenotype results.

Plants having inherited a transgene comprising a mutated EPSPS gene may be directly treated with the herbicide glyphosate without the result of significant damage to the plant. This phenotype provides farmers with the benefit of controlling weed growth in a field of plants having the herbicide resistance trait by application of the broad spectrum herbicide glyphosate. For example, one could apply the herbicide ROUNDUP™, a commercial formulation of glyphosate manufactured and sold by the Monsanto Company, over the top in fields where the glyphosate resistant soybeans are grown. The herbicide application rates may range from about 4 ounces of ROUNDUP™ to about 256 ounces ROUNDUP™ per acre. More preferably, about 16 ounces to about 64 ounces per acre of ROUNDUP™ may be applied to the field. However, the application rate may be increased or decreased as needed, based on the abundance and/or type of weeds being treated. Additionally, depending on the location of the field and weather conditions, which will influence weed growth and the type of weed infestation, it may be desirable to conduct further glyphosate treatments. The second glyphosate application will also typically comprise an application of about 16 ounces to about 64 ounces of ROUNDUP™ per acre treated. Again, the treatment rate may be adjusted based on field conditions. Such methods of application of herbicides to agricultural crops are well known in the art and are summarized in general in Anderson, 1983.

It will be understood to those of skill in the art that a herbicide resistance gene locus may be used for direct selection of plants having the resistance gene. For example, by applying about 16 to 64 ounces of ROUNDUP™ per acre to a collection of soybean plants which either have or lack the herbicide resistance trait, the plants lacking the trait will be killed or damaged. In this way, the herbicide resistant plants may be selected and used for commercial applications or advanced in certain breeding protocols. This application may find particular use during the breeding and development of herbicide resistant elite soybean varieties.

White flower color is an example of a recessive single locus trait. In this example, the progeny resulting from the first backcross generation ($BC_1$) are grown and selfed. The selfed progeny from the $BC_1$ plant are grown to determine which $BC_1$ plants carry the recessive gene for white flower color. In other recessive traits, additional progeny testing, for example growing additional generations such as the $BC_1F_2$, may be required to determine which plants carry the recessive gene.

Selection of soybean plants for breeding is not necessarily dependent on the phenotype of a plant and instead can be based on genetic investigations. For example, one may utilize a suitable genetic marker which is closely genetically linked to a trait of interest. One of these markers may therefore be used to identify the presence or absence of a trait in the offspring of a particular cross, and hence may be used in selection of progeny for continued breeding. This technique may commonly be referred to as marker assisted selection. Any other type of genetic marker or other assay which is able to identify the relative presence or absence of a trait of interest in a plant may also be useful for breeding purposes. Exemplary procedures for marker assisted selection which are applicable to the breeding of soybeans are disclosed in U.S. Pat. No. 5,437,697, and U.S. Pat. No. 5,491,081, both of which disclosures are specifically incorporated herein by reference in their entirety. Such methods will be of particular utility in the case of recessive traits and variable phenotypes, or where conventional assays are expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

Many qualitative characters also have potential use as phenotype-based genetic markers in soybeans; however, some or many may not differ among varieties commonly used as parents (Bernard and Weiss, 1973). The most widely used genetic markers are flower color (purple dominant to white), pubescence color (brown dominant to gray), and pod color (brown dominant to tan). The association of purple hypocotyl color with purple flowers and green hypocotyl color with white flowers is commonly used to identify hybrids in the seedling stage. Differences in maturity, height, hilum color, and pest resistance between parents can also be used to verify hybrid plants.

IV. ORIGIN AND BREEDING HISTORY OF AN EXEMPLARY SINGLE LOCUS CONVERTED PLANT

It is known to those of skill in the art that, by way of the technique of backcrossing, one or more traits may be introduced into a given variety while otherwise retaining essentially all of the traits of that variety. An example of a procedure for such backcrossing to introduce a trait into a starting variety is described in U.S. Pat. No. 6,140,556, the entire disclosure of which is specifically incorporated herein by reference. The procedure described in U.S. Pat. No. 6,140,556 can be summarized as follows: The soybean variety known as Williams "82 [*Glycine max* L. Merr.] (Reg. No. 222, PI 518671) was developed using backcrossing techniques to transfer a locus comprising the $Rps_1$ gene to the variety Williams (Bernard and Cremeens, 1988). Williams '82 is a composite of four resistant lines from the $BC_6F_3$ generation, which were selected from 12 field-tested resistant lines from Williams×Kingwa. The variety Williams was used as the recurrent parent in the backcross and the variety Kingwa was used as the source of the $Rps_1$ locus. This gene locus confers resistance to 19 of the 24 races of the fungal agent phytopthora rot.

The $F_1$ or $F_2$ seedlings from each backcross round were tested for resistance to the fungus by hypocotyl inoculation using the inoculum of race 5. The final generation was tested using inoculum of races 1 to 9. In a backcross such as this, where the desired characteristic being transferred to the recurrent parent is controlled by a major gene which can be readily evaluated during the backcrossing, it is common to conduct enough backcrosses to avoid testing individual progeny for specific traits such as yield in extensive replicated tests. In general, four or more backcrosses are used when there is no evaluation of the progeny for specific traits, such as yield. As in this example, lines with the phenotype of the recurrent parent may be composited without the usual replicated tests for traits such as yield, protein or oil percentage in the individual lines.

The variety Williams '82 is comparable to the recurrent parent variety Williams in all traits except resistance to phytopthora rot. For example, both varieties have a maturity of 38, indeterminate stems, white flowers, brown pubescence, tan pods at maturity and shiny yellow seeds with black to light black hila.

V. TISSUE CULTURES AND IN VITRO REGENERATION OF SOYBEAN PLANTS

A further aspect of the invention relates to tissue cultures of a soybean variety of the invention. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, pollen, flowers, leaves, roots, root tips, anthers, and the like. In a preferred embodiment, the tissue culture comprises embryos, protoplasts, meristematic cells, pollen, leaves or anthers.

Exemplary procedures for preparing tissue cultures of regenerable soybean cells and regenerating soybean plants therefrom, are disclosed in U.S. Pat. No. 4,992,375; U.S. Pat. No. 5,015,580; U.S. Pat. No. 5,024,944, and U.S. Pat. No. 5,416,011, each of the disclosures of which is specifically incorporated herein by reference in its entirety.

An important ability of a tissue culture is the capability to regenerate fertile plants. This allows, for example, transformation of the tissue culture cells followed by regeneration of transgenic plants. For transformation to be efficient and successful, DNA must be introduced into cells that give rise to plants or germ-line tissue.

Soybeans typically are regenerated via two distinct processes; shoot morphogenesis and somatic embryogenesis (Finer, 1996). Shoot morphogenesis is the process of shoot meristem organization and development. Shoots grow out from a source tissue and are excised and rooted to obtain an intact plant. During somatic embryogenesis, an embryo (similar to the zygotic embryo), containing both shoot and root axes, is formed from somatic plant tissue. An intact plant rather than a rooted shoot results from the germination of the somatic embryo.

Shoot morphogenesis and somatic embryogenesis are different processes and the specific route of regeneration is primarily dependent on the explant source and media used for tissue culture manipulations. While the systems are different, both systems show variety-specific responses where some lines are more responsive to tissue culture manipulations than others. A line that is highly responsive in shoot morphogenesis may not generate many somatic embryos. Lines that produce large numbers of embryos during an 'induction' step may not give rise to rapidly-growing proliferative cultures. Therefore, it may be desired to optimize tissue culture conditions for each soybean line. These optimizations may readily be carried out by one of skill in the art of tissue culture through small-scale culture studies. In addition to line-specific responses, proliferative cultures can be observed with both shoot morphogenesis and somatic embryogenesis. Proliferation is beneficial for both systems, as it allows a single, transformed cell to multiply to the point that it will contribute to germ-line tissue.

Shoot morphogenesis was first reported by Wright et al. (1986) as a system whereby shoots were obtained de novo from cotyledonary nodes of soybean seedlings. The shoot meristems were formed subepidermally and morphogenic tissue could proliferate on a medium containing benzyl adenine (BA). This system can be used for transformation if the subepidermal, multicellular origin of the shoots is recognized and proliferative cultures are utilized. The idea is to target tissue that will give rise to new shoots and proliferate those cells within the meristematic tissue to lessen problems associated with chimerism. Formation of chimeras, resulting from transformation of only a single cell in a meristem, are problematic if the transformed cell is not adequately proliferated and does not does not give rise to germ-line tissue. Once the system is well understood and reproduced satisfactorily, it can be used as one target tissue for soybean transformation.

Somatic embryogenesis in soybean was first reported by Christianson et al. (1983) as a system in which embryogenic tissue was initially obtained from the zygotic embryo axis. These embryogenic cultures were proliferative but the repeatability of the system was low and the origin of the embryos was not reported. Later histological studies of a different proliferative embryogenic soybean culture showed that proliferative embryos were of apical or surface origin with a small number of cells contributing to embryo formation. The origin of primary embryos (the first embryos derived from the initial explant) is dependent on the explant tissue and the auxin levels in the induction medium (Hartweck et al., 1988). With proliferative embryonic cultures, single cells or small groups of surface cells of the 'older' somatic embryos form the 'newer' embryos.

Embryogenic cultures can also be used successfully for regeneration, including regeneration of transgenic plants, if the origin of the embryos is recognized and the biological limitations of proliferative embryogenic cultures are understood. Biological limitations include the difficulty in developing proliferative embryogenic cultures and reduced fertility problems (culture-induced variation) associated with plants regenerated from long-term proliferative embryogenic cultures. Some of these problems are accentuated in prolonged cultures. The use of more recently cultured cells may decrease or eliminate such problems.

VI. GENETIC TRANSFORMATION OF SOYBEANS

Genetic transformation may be used to insert a selected transgene into a soybean variety of the invention or may, alternatively, be used for the preparation of transgenes which can be introduced into a soybean variety by backcrossing. Methods for the transformation of many economically important plants, including soybeans, are well know to those of skill in the art. Techniques which may be employed for the genetic transformation of soybeans include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

Protoplasts may also be employed for electroporation transformation of plants (Bates, 1994; Lazzeri, 1995). For example, the generation of transgenic soybean plants by electroporation of cotyledon-derived protoplasts was described by Dhir and Widholm in Intl. Patent Appl. Publ. No. WO 92/17598, the disclosure of which is specifically incorporated herein by reference.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target soybean cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species. The application of microprojectile bombardment for the transformation of soybeans is described, for example, in U.S. Pat. No. 5,322,783, the disclosure of which is specifically incorporated herein by reference in its entirety.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055). Use of *Agrobacterium* in the context of soybean transformation has been described, for example, by Chee and Slightom (1995) and in U.S. Pat. No. 5,569,834, the disclosures of which are specifically incorporated herein by reference in their entirety.

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). The demonstrated ability to regenerate soybean plants from protoplasts makes each of these techniques applicable to soybean (Dhir et al., 1991).

VII. UTILIZATION OF SOYBEAN PLANTS

A soybean plant provided by the invention may be used for any purpose deemed of value. Common uses include the preparation of food for human consumption, feed for non-human animal consumption and industrial uses. As used herein, "industrial use" or "industrial usage" refers to non-food and non-feed uses for soybeans or soy-based products.

Soybeans are commonly processed into two primary products, soybean protein (meal) and crude soybean oil. Both of these products are commonly further refined for particular uses. Refined oil products can be broken down into glycerol, fatty acids and sterols. These can be for food, feed or industrial usage. Edible food product use examples include coffee creamers, margarine, mayonnaise, pharmaceuticals, salad dressings, shortenings, bakery products, and chocolate coatings.

Soy protein products (e.g., meal), can be divided into soy flour concentrates and isolates which have both food/feed and industrial use. Soy flour and grits are often used in the manufacturing of meat extenders and analogs, pet foods, baking ingredients and other food products. Food products made from soy flour and isolate include baby food, candy products, cereals, food drinks, noodles, yeast, beer, ale, etc. Soybean meal in particular is commonly used as a source of protein in livestock feeding, primarily swine and poultry. Feed uses thus include, but are not limited to, aquaculture feeds, bee feeds, calf feed replacers, fish feed, livestock feeds, poultry feeds and pet feeds, etc.

Whole soybean products can also be used as food or feed. Common food usage includes products such as the seed, bean sprouts, baked soybean, full fat soy flour used in various products of baking, roasted soybean used as confectioneries, soy nut butter, soy coffee, and other soy derivatives of oriental foods. For feed usage, hulls are commonly removed from the soybean and used as feed.

Soybeans additionally have many industrial uses. One common industrial usage for soybeans is the preparation of binders that can be used to manufacture composites. For example, wood composites may be produced using modified soy protein, a mixture of hydrolyzed soy protein and PF resins, soy flour containing powder resins, and soy protein containing foamed glues. Soy-based binders have been used to manufacture common wood products such as plywood for over 70 years. Although the introduction of urea-formaldehyde and phenol-formaldehyde resins has decreased the usage of soy-based adhesives in wood products, environmental concerns and consumer preferences for adhesives made from a renewable feedstock have caused a resurgence of interest in developing new soy-based products for the wood composite industry.

Preparation of adhesives represents another common industrial usage for soybeans. Examples of soy adhesives include soy hydrolyzate adhesives and soy flour adhesives. Soy hydrolyzate is a colorless, aqueous solution made by reacting soy protein isolate in a 5 percent sodium hydroxide solution under heat (120° C.) and pressure (30 psig). The resulting degraded soy protein solution is basic (pH 11) and flowable (approximately 500 cps) at room temperature. Soy flour is a finely ground, defatted meal made from soybeans. Various adhesive formulations can be made from soy flour, with the first step commonly requiring dissolving the flour in a sodium hydroxide solution. The strength and other properties of the resulting formulation will vary depending on the additives in the formulation. Soy flour adhesives may also potentially be combined with other commercially available resins.

Soybean oil may find application in a number of industrial uses. Soybean oil is the most readily available and one of the lowest-cost vegetable oils in the world. Common industrial uses for soybean oil include use as components of anti-static agents, caulking compounds, disinfectants, fungicides, inks, paints, protective coatings, wallboard, anti-foam agents, alcohol, margarine, paint, ink, rubber, shortening, cosmetics, etc. Soybean oils have also for many years been a major ingredient in alkyd resins, which are dissolved in carrier solvents to make oil-based paints. The basic chemistry for converting vegetable oils into an alkyd resin under heat and pressure is well understood to those of skill in the art.

Soybean oil in its commercially available unrefined or refined, edible-grade state, is a fairly stable and slow-drying oil. Soybean oil can also be modified to enhance its reactivity under ambient conditions or, with the input of energy in various forms, to cause the oil to copolymerize or cure to a dry film. Some of these forms of modification have included epoxidation, alcoholysis or tranesterification, direct esterification, metathesis, isomerization, monomer modification, and various forms of polymerization, including heat bodying. The reactive linoleic-acid component of soybean oil with its double bonds is more useful than the more predominant oleic- and linoleic-acid components for many industrial uses.

Solvents can also be prepared using soy-based ingredients. For example, methyl soyate, a soybean-oil based methyl ester, is gaining market acceptance as an excellent solvent replacement alternative in applications such as parts cleaning and degreasing, paint and ink removal, and oil spill remediation. It is also being marketed in numerous formulated consumer products including hand cleaners, car waxes and graffiti removers. Methyl soyate is produced by the transesterification of soybean oil with methanol. It is commercially available from numerous manufacturers and suppliers. As a solvent, methyl soyate has important environmental- and safety-related properties that make it attractive for industrial applications. It is lower in toxicity than most other solvents, is readily biodegradable, and has a very high flash point and a low level of volatile organic compounds (VOCs). The compatibility of methyl soyate is excellent with metals, plastics, most elastomers and other organic solvents. Current uses of methyl soyate include cleaners, paint strippers, oil spill cleanup and bioremediation, pesticide adjuvants, corrosion preventives and biodiesel fuels additives.

VIII. DEFINITIONS

In the description and tables which follow, a number of terms are used. In order to provide a clear and consistent understanding of the specification and claims, the following definitions are provided:

A: When used in conjunction with the word "comprising" or other open language in the claims, the words "a" and "an" denote "one or more."

Agronomically Elite: As used herein, means a genotype that has a culmination of many distinguishable traits such as emergence, vigor, vegetative vigor, disease resistance, seed set, standability and threshability which allows a producer to harvest a product of commercial significance.

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Commercially Significant Yield: A yield of grain having commercial significance to the grower represented by an actual grain yield of at least 35 bushels per acre as a mean measured over at least 15 environments.

Crossing: The mating of two parent plants.

Cross-pollination: Fertilization by the union of two gametes from different plants.

Emergence: This is a score indicating the ability of a seed to emerge from the soil after planting. Each genotype is given a 1 to 9 score based on its percent of emergence. A score of 1 indicates an excellent rate and percent of emergence, an intermediate score of 5 indicates average ratings and a 9 score indicates a very poor rate and percent of emergence.

Enzymes: Molecules which can act as catalysts in biological reactions.

$F_1$ Hybrid: The first generation progeny of the cross of two nonisogenic plants.

Genotype: The genetic constitution of a cell or organism.

Industrial use: A non-food and non-feed use for a soybean plant. The term "soybean plant" includes plant parts and derivatives of a soybean plant.

Iron-Deficiency Chlorosis: A plant scoring system ranging from 1 to 9 based on visual observations. A score of 1 means no stunting of the plants or yellowing of the leaves and a score of 9 indicates the plants are dead or dying caused by iron-deficiency chlorosis, a score of 5 means plants have intermediate health with some leaf yellowing.

Linkage: A phenomenon wherein alleles on the same chromosome tend to segregate together more often than expected by chance if their transmission was independent.

Lodging Resistance: Lodging is rated on a scale of 1 to 9. A score of 1 indicates erect plants. A score of 5 indicates plants are leaning at a 45 degree(s) angle in relation to the ground and a score of 9 indicates plants are laying on the ground.

Marker: A readily detectable phenotype, preferably inherited in codominant fashion (both alleles at a locus in a diploid heterozygote are readily detectable), with no environmental variance component, i.e., heritability of 1.

Maturity Date: Plants are considered mature when 95% of the pods have reached their mature color. The maturity date is typically described in measured days after August 31 in the northern hemisphere.

Phenotype: The detectable characteristics of a cell or organism, which characteristics are the manifestation of gene expression.

*Phytophthora* Tolerance: Tolerance to *Phytophthora* root rot is rated on a scale of 1 to 9, with a score of 1 being the best or highest tolerance ranging down to a score of 9, which indicates the plants have no tolerance to *Phytophthora*.

Plant Height: Plant height is taken from the top of soil to the top node of the plant and is measured in inches.

Quantitative Trait Loci (QTL): Quantitative trait loci (QTL) refer to genetic loci that control to some degree numerically representable traits that are usually continuously distributed.

Regeneration: The development of a plant from tissue culture.

Relative Maturity: The maturity grouping designated by the soybean industry over a given growing area. This figure is generally divided into tenths of a relative maturity group. Within narrow comparisons, the difference of a tenth of a relative maturity group equates very roughly to a day difference in maturity at harvest.

Seed Protein Peroxidase Activity. Seed protein peroxidase activity is defined as a chemical taxonomic technique to separate varieties based on the presence or absence of the peroxidase enzyme in the seed coat. There are two types of soybean varieties, those having high peroxidase activity (dark red color) and those having low peroxidase activity (no color).

Self-pollination: The transfer of pollen from the anther to the stigma of the same plant.

Shattering: The amount of pod dehiscence prior to harvest. Pod dehiscence involves seeds falling from the pods to the soil. This is a visual score from 1 to 9 comparing all genotypes within a given test. A score of 1 means pods have not opened and no seeds have fallen out. A score of 5 indicates approximately 50% of the pods have opened, with seeds falling to the ground and a score of 9 indicates 100% of the pods are opened.

Single Locus Converted (Conversion) Plant: Plants which are developed by a plant breeding technique called backcrossing, wherein essentially all of the desired morphological and physiological characteristics of a soybean variety are recovered in addition to the characteristics of the single locus transferred into the variety via the backcrossing technique and/or by genetic transformation.

Substantially Equivalent: A characteristic that, when compared, does not show a statistically significant difference (e.g., $p=0.05$) from the mean.

Tissue Culture: A composition comprising isolated cells of the same or a different type or a collection of such cells organized into parts of a plant.

Transgene: A genetic locus comprising a sequence which has been introduced into the genome of a soybean plant by transformation.

IX. DEPOSIT INFORMATION

A deposit of the seed of soybean variety 0007583, which has been described herein, has been made with the American Type Culture Collection (ATCC), 10801 University Blvd., Manassas, Va. 20110-2209. The date of deposit was Jan. 14, 2004. The accession number for those deposited seeds is ATCC Accession No. PTA-5764.

A deposit of the seed of soybean variety 0008079, which has been described herein, has been made with the American Type Culture Collection (ATCC), 10801 University Blvd., Manassas, Va. 20110-2209. The date of deposit was May 18, 2006. The accession number for those deposited seeds is ATCC Accession No. PTA-7601.

A deposit of the seed of soybean variety 0137335, which has been described herein, has been made with the American Type Culture Collection (ATCC), 10801 University Blvd., Manassas, VA 20110-2209. The date of deposit was Jan. 4, 2007. The accession number for those deposited seeds in ATCC Accession No. PTA-8110.

A deposit of the seed of soybean variety SN30017, which has been described herein, has been made with the American Type Culture Collection (ATCC), 10801 University Blvd., Manassas, Va. 20110-2209. The date of deposit was _____. The accession number for those deposited seeds is ATCC Accession No. _____.

A deposit of the seed of soybean variety A2552, which has been described herein, has been made with the American Type Culture Collection (ATCC), 10801 University Blvd., Manassas, Va. 20110-2209. The date of deposit was _____. The accession number for those deposited seeds is ATCC Accession No. _____.

A deposit of the seed of soybean variety AGW26703, which has been described herein, has been made with the American Type Culture Collection (ATCC), 10801 University Blvd., Manassas, Va. 20110-2209. The date of deposit was _____. The accession number for those deposited seeds is ATCC Accession No. _____.

A deposit of the seed of soybean variety AG3003, which has been described herein, has been made with the American Type Culture Collection (ATCC), 10801 University Blvd., Manassas, Va. 20110-2209. The date of deposit was _____. The accession number for those deposited seeds is ATCC Accession No. _____.

A deposit of the seed of soybean variety AG3302, which has been described herein, has been made with the American Type Culture Collection (ATCC), 10801 University Blvd., Manassas, Va. 20110-2209. The date of deposit was _____. The accession number for those deposited seeds is ATCC Accession No. _____.

All restrictions upon each of the foregoing deposits have been removed, and the deposits are intended to meet all of the requirements of 37 C.F.R. §1.801–1.809. The deposits will be maintained in the depository for a period of 30 years, or 5 years after the last request, or for the effective life of the patent, whichever is longer, and will be replaced if necessary during that period.

X. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Development of Soybean Variety 0007583

The instant invention provides methods and composition relating to plants, seeds and derivatives of the soybean variety 0007583. Soybean variety 0007583 is adapted to the mid-group 2 soybean growing region, is resistant to multiple *Phytophthora* races and exhibits high seed protein and protein plus oil in combination with high yield. The variety was derived from an initial cross of soybean varieties A2553 and SN30003. The variety was developed as follows: The original cross of A2553 and SN30003 was made at Isabella, PR during the winter of 1996–97. F1 seed was grown at Janesville, Wis. in 1997 and F2 seed was grown at Isabella, PR during the winter of 1997–98. Bulked F3 seed was grown at Janesville, Wis. in 1998 and single plant selections were made from the bulk population and threshed individually. F3:4 seed was planted in PRYT (Single Plant Yield Test) in 1999 at Janesville, Wis. F3:5 seed was planted at 5 locations in Wisconsin in 2000 to test for yield and genotype while breeder seed was grown at Beaman, Iowa. F3:6 seed was planted at 11 locations throughout the Midwest in 2001 to test for yield and genotype while breeder seed was increased at Beaman, Iowa. Some of the criteria used to select the variety in various generations include: seed yield, lodging resistance, emergence, seedling vigor, disease tolerance, maturity, plant height and seed oil and protein content.

The soybean variety 0007583 has been judged to be uniform for breeding purposes and testing. The variety 0007583 can be reproduced by planting and growing seeds of the variety under self-pollinating or sib-pollinating conditions, as is known to those of skill in the agricultural arts. Variety 0007583 shows no variants other than what would normally be expected due to environment or that would occur for almost any characteristic during the course of repeated sexual reproduction. The results of an objective description of the variety are presented below, in Table 1. Those of skill in the art will recognize that these are typical values that may vary due to environment and that other values that are substantially equivalent are within the scope of the invention.

TABLE 1

| Phenotypic Description of Variety 0007583 | |
|---|---|
| Trait | Phenotype |
| Relative Maturity | 2.7 |
| Roundup Ready | Suscept. |
| STS | Suscept. |
| Liberty | Suscept. |
| Flower | Purple |
| Pubescence | Gray |

TABLE 1-continued

Phenotypic Description of Variety 0007583

| Trait | Phenotype |
|---|---|
| Hilum | Imperfect Black |
| Pod Color | Tan |
| Seed Luster | Dull |
| Hypocotyl Color | Light Purple |
| Seed Shape | Spherical Flattened |
| Leaf Shape | Ovate |
| Leaflet Size | Medium |
| Leaf Color | Medium |
| Canopy | Bushy |
| Growth Habit | Indeterminate |
| Phytophthora Allele | $Rpsl^k$ |
| SCN Race 3 | Susc. |
| SCN Race 14 | Susc. |
| Area of adaptation: | Mid-group 2 soybean growing region. |
| PRR tolerance score | 4.7 (test average of 4.7) |
| IDC composite score | 4.3 (test average of 4.7). |

The performance characteristics of soybean variety 0007583 were analyzed and comparisons were made with competing varieties. Characteristics examined included maturity, plant height, lodging, seed protein and oil content and iron deficiency chlorosis rating. The results of the analysis are presented below, in Tables 2–7.

TABLE 2

Exemplary Agronomic Traits of Variety 0007583 and Selected Varieties

| Variety | Mat | Ht | Lodg | Protein | Oil |
|---|---|---|---|---|---|
| 0007583 | 24.5 | 37.5 | 2.5 | 46.2 | 20.4 |
| A2247 | 23.0 | 34.5 | 2.5 | 43.3 | 21.6 |
| A2553 | 24.5 | 31.0 | 2.5 | 40.2 | 23.0 |
| A2824 | 29.0 | 33.0 | 3.0 | 44.0 | 21.2 |
| SN30003 | 24.5 | 37.0 | 2.5 | 51.0 | 18.5 |
| SN30017 | 27.5 | 42.0 | 3.0 | 49.1 | 19.7 |

TABLE 3

Iron Deficiency Chlorosis Rating for Variety 0007583 and Selected Varieties

| Variety | IDE | IDC | Mean |
|---|---|---|---|
| 0007583 | 4.7 | 6.3 | 5.5 |
| A1923 | 3.3 | 4.0 | 3.7 |
| A2247 | 4.7 | 4.5 | 4.6 |
| A2553 | 4.7 | 5.0 | 4.8 |
| Mean | 4.4 | 5.0 | 4.7 |
| Range | 2.7–6.2 | 2.8–7.2 | 2.8–6.5 |

IDE = Early iron deficiency chlorosis rating
IDC = Iron deficiency chlorosis rating

TABLE 4

Yield Testing for Variety 0007583

| Gen. | Year | Test-Entry | # locs | Rank | # Entries |
|---|---|---|---|---|---|
| $F_4$ | 1999 | 9WY37M-02 | 1 | 13 | 48 |
| $F_5$ | 2000 | 00JWIX-10 | 5 | 01 | 50 |
| $F_6$ | 2001 | 01JWH0-21 | 11 | 32 | 50 |

TABLE 5

Head to Head Comparisons of Variety 0007583 (Check) Versus Listed Others: All Year, All Location

| VARIETY | TST | WINS | BU/AC CHK | BU/AC CMP | DIFF | MAT # TST | MAT CHK | MAT CMP | IDE # TST | IDE CHK | IDE CMP |
|---|---|---|---|---|---|---|---|---|---|---|---|
| AG2102-14 | 11 | 9 | 47.4 | 43.9 | 3.5 | 9 | 25.6 | 20.6 | 2 | 4.3 | 4.8 |
| AG2202 | 11 | 7 | 47.4 | 47.2 | 0.2 | 9 | 25.6 | 24.3 | 2 | 4.3 | 4.8 |
| A2247 | 15 | 10 | 49.4 | 47.1 | 2.3 | 11 | 25.4 | 22.6 | 2 | 4.3 | 4.8 |
| AG2402 | 11 | 7 | 47.4 | 45.3 | 2.1 | 9 | 25.6 | 23.8 | 2 | 4.3 | 4.1 |
| A2553 | 15 | 2 | 49.4 | 53.0 | -3.6 | 11 | 25.4 | 25.4 | 2 | 4.3 | 4.4 |
| CSR2310 | 11 | 3 | 47.4 | 48.4 | -1.0 | 9 | 25.6 | 24.6 | 2 | 4.3 | 4.6 |
| CST21000 | 11 | 4 | 47.4 | 49.5 | -2.1 | 9 | 25.6 | 24.4 | 2 | 4.3 | 4.8 |
| CST23000 | 11 | 2 | 47.4 | 50.4 | -3.0 | 9 | 25.6 | 26.1 | 2 | 4.3 | 4.4 |
| CST231N | 11 | 4 | 47.4 | 48.5 | -1.1 | 9 | 25.6 | 23.2 | 2 | 4.3 | 4.3 |
| MBS59125 | 11 | 3 | 47.4 | 49.1 | -1.7 | 9 | 25.6 | 29.3 | 2 | 4.3 | 4.3 |
| NKS24-L2 | 11 | 5 | 47.4 | 48.4 | -1.0 | 9 | 25.6 | 22.5 | 2 | 4.3 | 3.6 |
| PION92B23 | 11 | 5 | 47.4 | 48.1 | -0.6 | 9 | 25.6 | 21.9 | 2 | 4.3 | 3.8 |
| PION92B35 | 11 | 4 | 47.4 | 47.8 | -0.3 | 9 | 25.6 | 23.1 | 2 | 4.3 | 5.4 |

| VARIETY | OIL # TST | OIL CHK | OIL CMP | PRO # TST | PRO CHK | PRO CMP | PHT # TST | PHT CHK | PHT CMP | LDG # TST | LDG CHK | LDG CMP |
|---|---|---|---|---|---|---|---|---|---|---|---|---|
| AG2102-14 | 4 | 20.9 | 22.2 | 4 | 44.3 | 40.0 | 6 | 37.0 | 31.8 | 9 | 1.9 | 1.3 |
| AG2202 | 4 | 20.9 | 21.4 | 4 | 44.3 | 40.3 | 6 | 37.0 | 34.3 | 9 | 1.9 | 1.2 |
| A2247 | 7 | 20.8 | 22.0 | 7 | 44.8 | 41.9 | 8 | 37.1 | 35.4 | 11 | 2.0 | 2.0 |
| AG2402 | 4 | 20.9 | 22.1 | 4 | 44.3 | 40.8 | 6 | 37.0 | 35.3 | 9 | 1.9 | 1.6 |
| A2553 | 7 | 20.8 | 23.1 | 7 | 44.8 | 38.9 | 8 | 37.1 | 33.1 | 11 | 2.0 | 1.8 |
| CSR2310 | 4 | 20.9 | 21.5 | 4 | 44.3 | 40.7 | 6 | 37.0 | 33.5 | 9 | 1.9 | 1.5 |
| CST21000 | 4 | 20.9 | 22.2 | 4 | 44.3 | 40.4 | 6 | 37.0 | 31.3 | 9 | 1.9 | 1.2 |
| CST23000 | 4 | 20.9 | 21.7 | 4 | 44.3 | 40.1 | 6 | 37.0 | 35.1 | 9 | 1.9 | 1.4 |
| CST231N | 4 | 20.9 | 21.8 | 4 | 44.3 | 41.6 | 6 | 37.0 | 33.6 | 9 | 1.9 | 1.4 |
| MBS59125 | 4 | 20.9 | 20.4 | 4 | 44.3 | 40.9 | 6 | 37.0 | 35.2 | 9 | 1.9 | 1.9 |

TABLE 5-continued

Head to Head Comparisons of Variety 0007583 (Check) Versus Listed Others: All Year, All Location

| NKS24-L2 | 4 | 20.9 | 21.9 | 4 | 44.3 | 39.9 | 6 | 37.0 | 32.2 | 9 | 1.9 | 1.6 |
| PION92B23 | 3 | 21.0 | 22.7 | 3 | 43.9 | 38.9 | 6 | 37.0 | 31.4 | 9 | 1.9 | 1.8 |
| PION92B35 | 4 | 20.9 | 22.0 | 4 | 44.3 | 40.8 | 6 | 37.0 | 35.4 | 9 | 1.9 | 2.2 |

TST = Research - No. of tests
WINS = Number of wins versus listed varieties
BU/AC = Yield (bushels/acre)
MAT = Maturity (days)
IDE = Iron deficiency chlorosis (early) rating
OIL = Seed oil content
PRO = Seed protein content
PHT = Plant Height (inches)
LDG = Lodging Rating (scale: 1–9, 1 = best)

TABLE 6

Performance Comparison of Variety 0007583 Versus Competing Varieties

| Variety | YLD | MAT DAY | PLT HGT | LDG | PHO SCR | FLD EMR | IDC | % PRO | % OIL |
|---|---|---|---|---|---|---|---|---|---|
| 0007583 | 47.4 | 25.6 | 37.0 | 1.9 | 3.3 | 1.3 | 4.3 | 43.8 | 21.2 |
| ASGROW A2553 | 52.9 | 25.6 | 33.8 | 1.6 | 2.5 | 1.8 | 4.4 | 38.8 | 23.1 |
| DEKALB DKB23-95 | 51.3 | 25.4 | 33.5 | 1.5 | 3.0 | 1.3 | 5.1 | 42.2 | 21.4 |
| STINE 2491-6 | 50.8 | 26.7 | 32.5 | 1.4 | 2.9 | 1.7 | 4.8 | 42.1 | 21.2 |
| CORN STATES T23000 | 50.4 | 26.1 | 35.1 | 1.4 | 2.8 | 1.3 | 4.4 | 40.3 | 21.9 |
| CORN STATES T21000 | 49.5 | 24.4 | 31.3 | 1.2 | 2.5 | 1.5 | 4.8 | 40.6 | 22.3 |
| MIKE BRAYTON SEEDS 59125 | 49.1 | 29.3 | 35.2 | 1.9 | 2.9 | 1.3 | 4.3 | 41.2 | 20.5 |
| PIONEER 92B37 | 48.5 | 22.0 | 39.4 | 2.1 | 3.8 | 1.7 | 4.2 | 40.8 | 22.4 |
| DEKALB DKB23-73 | 48.5 | 23.2 | 33.6 | 1.4 | 2.9 | 1.2 | 4.3 | 41.9 | 21.9 |
| DEKALB DKB23-51 | 48.4 | 24.6 | 33.5 | 1.5 | 2.9 | 2.0 | 4.6 | 41.0 | 21.6 |
| SYNGENTA NKS24-L2 | 48.4 | 22.5 | 32.2 | 1.6 | 3.2 | 1.2 | 3.6 | 40.1 | 22.0 |
| PIONEER 92B23 | 48.1 | 21.9 | 31.4 | 1.8 | 3.2 | 1.3 | 3.8 | 39.5 | 22.7 |
| PIONEER 92B35 | 47.8 | 23.1 | 35.4 | 2.2 | 2.8 | 1.5 | 5.4 | 41.0 | 22.1 |
| ASGROW AG2202 | 47.2 | 24.3 | 34.3 | 1.2 | 2.4 | 1.8 | 4.8 | 40.6 | 21.5 |
| ASGROW A2247 | 46.2 | 22.5 | 35.8 | 1.9 | 3.5 | 1.5 | 4.8 | 41.9 | 22.2 |
| STINE 1892-2 | 46.0 | 18.2 | 31.1 | 2.3 | 3.7 | 1.7 | 4.2 | 40.6 | 22.7 |
| SYNGENTA NKS21-A1 | 45.9 | 17.6 | 31.6 | 1.8 | 3.3 | 2.0 | 5.2 | 40.3 | 23.0 |
| HISOY 10C2-1-2 | 45.5 | 19.8 | 34.1 | 2.0 | 3.6 | 1.4 | 5.0 | 40.5 | 21.7 |
| IVORY | 45.3 | 20.6 | 29.5 | 1.2 | 3.3 | 1.3 | 4.8 | 41.6 | 22.2 |
| HISOY 10C2-1-3 | 45.3 | 18.9 | 36.9 | 1.9 | 3.6 | 1.5 | 4.1 | 40.6 | 21.8 |
| ASGROW AG2402 | 45.3 | 23.8 | 35.3 | 1.6 | 2.7 | 1.5 | 4.1 | 41.0 | 22.2 |
| HISOY 10C2-13-2 | 45.1 | 25.1 | 34.2 | 2.1 | 3.3 | 1.0 | 4.5 | 41.2 | 22.2 |
| ASGROW A2069 | 45.0 | 18.0 | 30.5 | 1.6 | 3.2 | 1.3 | 3.8 | 41.4 | 21.7 |
| ASGROW A1923 | 44.5 | 17.3 | 31.8 | 1.2 | 2.9 | 1.5 | 4.7 | 40.6 | 22.0 |
| ASGROW AG2001 | 43.7 | 18.3 | 32.3 | 1.6 | 2.9 | 1.2 | 5.1 | 41.2 | 23.0 |
| DEKALB DKB19-51 | 42.3 | 18.3 | 32.0 | 1.2 | 2.8 | 2.2 | 4.1 | 39.5 | 22.6 |
| ENTRY MEAN | 48.2 | 23.3 | 33.9 | 1.8 | 3.1 | 1.5 | 4.7 | 40.9 | 21.9 |
| LSD (.30) | 1.4 | 0.8 | 1.1 | 0.3 | 0.3 | 0.4 | 0.8 | 0.4 | 0.2 |
| LSD (.05) | 2.7 | 1.6 | 2.1 | 0.6 | 0.6 | 0.8 | 1.5 | 0.8 | 0.4 |
| CV | 6.7 | 7.3 | 5.4 | 34.3 | 19.0 | 34.3 | 16.5 | 1.5 | 1.4 |
| # of TESTS | 11.0 | 9.0 | 6.0 | 9.0 | 8.0 | 3.0 | 2.0 | 5.0 | 5.0 |

TABLE 7

Additional Comparison of 0007583 With Selected Varieties Over 5 Locations

| Variety | YLD | MAT DATE | PLT HGT | LDG | PHO SCR | % PRO | % OIL |
|---|---|---|---|---|---|---|---|
| 0007583 | 54.7 | 24.5 | 37.5 | 2.5 | 4.5 | 46.2 | 20.4 |
| ASGROW A2553 | 53.1 | 24.5 | 31.0 | 2.5 | 3.5 | 40.2 | 23.0 |
| ASGROW A2247 | 49.7 | 23.0 | 34.5 | 2.5 | 3.5 | 43.3 | 21.6 |
| ASGROW A2824 | 49.5 | 29.0 | 33.0 | 3.0 | 5.0 | 44.0 | 21.2 |
| SN30017 | 46.7 | 27.5 | 42.0 | 3.0 | 5.5 | 49.1 | 19.7 |
| SN30003 | 44.4 | 24.5 | 37.5 | 2.5 | 5.0 | 50.5 | 18.7 |
| ENTRY MEAN | 45.8 | 25.1 | 37.0 | 2.6 | 4.9 | 47.0 | 19.7 |
| LSD (.30) | 2.8 | 1.3 | 1.9 | 0.5 | 0.7 | 0.8 | 0.4 |
| LSD (.05) | 5.3 | 2.4 | 3.7 | 1.0 | 1.3 | 1.5 | 0.7 |
| CV | 8.2 | 4.8 | 5.0 | 19.3 | 12.8 | 2.2 | 2.5 |
| # of TESTS | 4.0 | 2.0 | 2.0 | 2.0 | 2.0 | 4.0 | 4.0 |

Example 2

Development of Soybean Variety 0008079

The soybean variety 0008079 is a glyphosate tolerant variety exhibiting high seed protein and protein plus oil in combination with high yield and an agronomically elite background. The variety exhibits resistance to multiple races of *Phytophthora* from Rps1$^k$ allele. The variety is adapted to mid-Group 2 soybean growing regions and has a relative maturity of 2.8. The variety was derived from an initial cross of the soybean varieties SN30003 and AGW26703 made at Isabella, PR during winter 1996–97. The variety was developed as follows: F1 seed was grown at Janesville, Wis. in 1997 and F2 seed at Isabella, PR during winter 1997–98. Bulked F3 seed was grown at Janesville, Wis. in 1998 and single plant selections were made from the bulk population and threshed individually. F3:4 seed was planted in PRYT (Single Plant Yield Test) in 1999 at Janesville, Wis. F3:5 seed was planted at 5 locations in Wisconsin in 2000 to test for yield and genotype while breeder seed was grown at Beaman, Iowa. F3:6 seed was planted at 10 locations throughout the Midwest in 2001 to test for yield and genotype while breeder seed was increased at Beaman, Iowa. Some of the criteria used to select the variety in various generations included: yield, lodging resistance, emergence, seedling vigor, disease tolerance, maturity, plant height, seed oil and protein content.

The soybean variety 0008079 has been judged to be uniform for breeding purposes and testing. The variety 0008079 can be reproduced by planting and growing seeds of the variety under self-pollinating or sib-pollinating conditions, as is known to those of skill in the agricultural arts. Variety 0008079 shows no variants other than what would normally be expected due to environment or that would occur for almost any characteristic during the course of repeated sexual reproduction. The results of an objective description of the variety are presented below, in Table 8. Those of skill in the art will recognize that these are typical values that may vary due to environment and that other values that are substantially equivalent are within the scope of the invention.

TABLE 8

Phenotypic Description of Variety 0008079

| Trait | Phenotype |
|---|---|
| Relative Maturity | 2.6 |
| Roundup Ready | RR |
| STS | Susc. |
| Liberty | Susc. |
| Flower | Purple |
| Pubescence | Gray |
| Hilum BL/BR/Y/G/IB/BF/M | Imp. Black |
| Pod Color | Brown |
| Seed Luster | Dull |
| Hypocotyl Color | Light Purple |
| Seed Shape | Spher. Flattened |
| Leaf Shape | Ovate |
| Leaflet Size | Medium |
| Leaf Color | Medium |

TABLE 8-continued

Phenotypic Description of Variety 0008079

| Trait | Phenotype |
|---|---|
| Canopy | Bushy |
| Growth Habit (I/D/S)* | Indeterm. |
| Phytophthora Allele | Rps1$^k$ |
| SCN Race 3 | Susc. |
| SCN Race 14 | Susc. |

The performance characteristics of soybean variety 0008079 were also analyzed and comparisons were made with competing varieties. Characteristics examined included maturity, plant height, lodging, resistance to *Phytophthora* Root Rot, yield, seed protein and oil content. The results of the analysis are presented below, in Tables 9–13.

TABLE 9

Exemplary Agronomic Traits of Variety 0008079 and Selected Varieties

AGRONOMIC CHARACTERISTICS

| Lines | Mat Date | Ht | Lodg | Protein | Oil |
|---|---|---|---|---|---|
| 0008079 | 26.0 | 32.0 | 2.0 | 48.1 | 18.9 |
| AG2402 | 15.6 | 33.6 | 1.2 | 41.0 | 22.3 |
| AG2703 | 22.6 | 35.1 | 1.1 | 40.1 | 22.0 |
| DKB26-52 | 21.0 | 39.1 | 3.7 | 41.4 | 21.6 |
| SN30003 | 24.5 | 37.0 | 2.5 | 51.0 | 18.5 |
| SN30017 | 27.5 | 42.0 | 3.0 | 49.1 | 19.7 |

TABLE 10

Yield Testing for Variety 0008079

| Gen. | Year | Test-Entry | # locs | Rank | # Entries |
|---|---|---|---|---|---|
| F$_4$ | 1999 | 9WY38R-37 | 1 | 1 | 48 |
| F$_5$ | 2000 | 00JWIX-39 | 5 | 6 | 50 |
| F$_6$ | 2001 | 01JWI3-26 | 10 | 49 | 50 |

TABLE 11

Analysis of (tested reactions) *Phytophthora* Root Rot Reaction (*Phytophthora megasperma* var. *sojae*)*

| Test Entry | Race | Ratio Dead | Total |
|---|---|---|---|
| 01JWI3-26 | 1 | 0 | 15 |
| 01JWI3-26 | 3 | 0 | 14 |
| 01JWI3-26 | 5 | 0 | 13 |

*Probable Resistance to Races: 1–11, 13–15, 17, 18, 21–24, 26, 27, 36–38

TABLE 12

Performance Comparison Of Variety 0008079 Versus Competing Varieties Over 10 Locations

| Variety | YLD | MAT DATE | PLT HGT | LDG | PHO SCR | FLD EMR | % PRO | % OIL |
|---|---|---|---|---|---|---|---|---|
| 0008079 | 40.1 | 27.1 | 36.3 | 2.0 | 3.6 | 1.2 | 48.1 | 19.0 |
| DEKALB DKB26-52 | 47.0 | 21.0 | 39.1 | 3.7 | 4.6 | 1.2 | 41.2 | 21.9 |
| ASGROW AG2703 | 46.8 | 22.6 | 35.1 | 1.1 | 3.0 | 1.0 | 40.1 | 22.2 |
| ASGROW AG2402 | 43.1 | 15.6 | 33.6 | 1.2 | 2.9 | 1.0 | 40.8 | 22.6 |
| ASGROW DJW2601E0R | 37.7 | 23.6 | 36.9 | 2.4 | 4.4 | 1.2 | | |
| ENTRY MEAN | 44.6 | 22.3 | 35.6 | 1.9 | 3.5 | 1.1 | 42.6 | 21.4 |

TABLE 12-continued

Performance Comparison Of Variety 0008079 Versus Competing Varieties Over 10 Locations

| Variety | YLD | MAT DATE | PLT HGT | LDG | PHO SCR | FLD EMR | % PRO | % OIL |
|---|---|---|---|---|---|---|---|---|
| LSD (.30) | 1.3 | 0.8 | 1.0 | 0.3 | 0.4 | 0.2 | 0.2 | 0.1 |
| LSD (.05) | 2.5 | 1.4 | 2.0 | 0.6 | 0.8 | 0.5 | 0.4 | 0.2 |
| CV | 6.5 | 7.0 | 5.2 | 27.6 | 21.8 | 20.1 | 0.9 | 0.9 |
| # of TESTS | 10.0 | 9.0 | 7.0 | 5.0 | 8.0 | 2.0 | 6.0 | 6.0 |

TABLE 13

Additional Comparison of 0008079 With Selected Varieties Over 5 locations

| Variety | YLD | MAT DATE | PLT HGT | LDG | PHO SCR | % PRO | % OIL |
|---|---|---|---|---|---|---|---|
| 0008079 | 49.2 | 26.0 | 32.0 | 2.0 | 4.5 | 48.4 | 18.9 |
| A2553 | 53.1 | 24.5 | 31.0 | 2.5 | 3.5 | 40.2 | 23.0 |
| A2247 | 49.7 | 23.0 | 34.5 | 2.5 | 3.5 | 43.3 | 21.6 |
| A2824 | 49.5 | 29.0 | 33.0 | 3.0 | 5.0 | 44.0 | 21.2 |
| SN30017 | 46.7 | 27.5 | 42.0 | 3.0 | 5.5 | 49.1 | 19.7 |
| SN30003 | 44.4 | 24.5 | 37.5 | 2.5 | 5.0 | 50.5 | 18.7 |
| ENTRY MEAN | 45.8 | 25.1 | 37.0 | 2.6 | 4.9 | 47.0 | 19.7 |
| CHECK MEAN | 47.8 | 25.5 | 35.7 | 2.7 | 4.6 | 46.4 | 20.4 |
| LSD (.30) | 2.8 | 1.3 | 1.9 | 0.5 | 0.7 | 0.8 | 0.4 |
| LSD (.05) | 5.3 | 2.4 | 3.7 | 1.0 | 1.3 | 1.5 | 0.7 |
| CV | 8.2 | 4.8 | 5.0 | 19.3 | 12.8 | 2.2 | 2.5 |
| # of TESTS | 4.0 | 2.0 | 2.0 | 2.0 | 2.0 | 4.0 | 4.0 |

Example 3

Development of Soybean Variety 0137335

Soybean variety 0137335 is resistant to glyphosate and exhibits high seed protein and protein plus oil in combination with high yield and an agronomically elite background. The soybean variety 0137335 is adapted to the Iowa, mid-Illinois & mid-Indiana growing region and has a maturity of 23. The variety was derived from an initial cross of soybean varieties SN30003 and AG3003 made at Ames, Iowa in 1998. The variety was developed as follows: F1 and F2 seed were grown at Isabela, PR in the fall of 1998 and late winter of 1999. F2 plants were selected and threshed individually. F2:3 seed was planted in a PROW (Progeny Row) plot in 1999 at Ames, Iowa. The F3 plants were selected and threshed individually from PROW plots exhibiting the best agronomic characteristics. The seed from each F3 plant was analyzed for protein content. The F3:4 lines with the highest protein content were planted in PROW plots at Ames, Iowa in 2000.

In the fall of 2000, lines with the best agronomic characteristics were harvested in bulk. Of these, the lines with the highest grain protein levels were selected for 2001 yield testing. F3:5 seed was planted at 5 locations in Iowa to test for yield and agronomic performance. Breeder seed increase will be grown in 2002 at Beaman, Iowa. Some of the criteria used to select the variety in various generations included: yield, lodging resistance, emergence, seedling vigor, disease tolerance, maturity, plant height, seed oil and protein content.

The results of an objective description of the variety produced are presented below, in Table 14. Those of skill in the art will recognize that these are typical values that may vary due to environment and that other values that are substantially equivalent are within the scope of the invention.

TABLE 14

Phenotypic Description of Variety 0137335

| Trait | Phenotype |
|---|---|
| Relative Maturity | 2.3 |
| Roundup Ready | RR |
| STS | Susceptible |
| Liberty | Susceptible |
| Flower | Purple |
| Pubescence | Gray |
| Hilum | Imperfect Black |
| Pod Color | |
| Seed Luster D/S/M | |
| Hypocotyl Color | |
| Seed Shape | Spherical Flattened |
| Leaf Shape | Ovate |
| Leaflet Size | Medium |
| Leaf Color | Medium |
| Canopy | |
| Growth Habit | Indeterminate |
| Phytophthora Allele | |
| SCN Race 3 | Susceptible |
| SCN Race 14 | Susceptible |
| Root Knot Nematode | Susceptible |

The performance characteristics of soybean variety 0137335 were analyzed and comparisons were made with competing varieties. Characteristics examined included maturity, plant height, lodging, seed protein and seed oil content. The results of the analysis are presented below, in Tables 15–17.

TABLE 15

Exemplary Agronomic Traits of Variety 0137335 and Selected Varieties

| | AGRONOMIC CHARACTERISTICS | | | | | |
|---|---|---|---|---|---|---|
| Lines | Mat Date | Ht | Lodg | Protein | Oil | Seed/lb |
| 0137335 | 25 | | 3.3 | 43.9 | 20.9 | |
| DKB23-51 | 24 | | 2.5 | 39.9 | 21.7 | |
| AG2103 | 22 | | 2.0 | 40.3 | 21.8 | |

TABLE 16

Yield Testing for Variety 0137335

| Gen. | Year | Test-Entry | # locs | Rank | # Entries |
|---|---|---|---|---|---|
| F$_{3:5}$ | 2001 | 01AHHA-10 | 5 | 6 | 50 |

TABLE 17

Performance Comparison Of Variety 0137335 Versus Competing Varieties Over 5 Locations

| Variety | YLD | % OIL | % PRO | MAT DATE | LDG | PLT HGT | FLD EMR | PHO SCR |
|---|---|---|---|---|---|---|---|---|
| 0137335 | 48.3 | 20.9 | 43.9 | 24.6 | 3.3 | | 3.0 | 3.3 |
| DKB23-51 | 53.8 | 21.7 | 39.9 | 24.0 | 2.5 | 37.0 | 2.0 | 3.5 |
| AG2103 | 52.2 | 21.8 | 40.3 | 21.6 | 2.0 | 36.0 | 3.0 | 2.5 |
| CX198RR | 47.6 | 21.5 | 40.4 | 21.0 | 2.0 | 36.0 | 3.0 | 3.3 |
| A2553/AG1901:63.@. | 45.0 | 24.9 | 36.0 | 19.0 | 2.5 | 33.0 | 2.0 | 2.8 |
| AG1901 | 41.9 | 24.4 | 37.8 | 19.0 | 3.5 | 46.0 | 3.0 | 4.3 |
| ENTRY MEAN | 43.5 | 21.4 | 42.4 | 22.6 | 2.8 | 36.3 | 4.1 | 3.5 |
| LSD (.30) | 2.5 | 0.3 | 0.5 | 1.0 | 0.6 | | 0.4 | 0.7 |
| LSD (.05) | 4.8 | 0.5 | 0.9 | 2.0 | 1.1 | | 1.0 | 1.3 |
| # of TESTS | 5.0 | 5.0 | 5.0 | 5.0 | 3.0 | 3.0 | 3.0 | 4.0 |

Example 4

Development of Soybean Variety 0137472

The variety 0137472 is adapted to the Iowa, mid-Illinois & mid-Indiana growing region and has a maturity of 24. The variety is glyphosate resistant and exhibits high seed protein and protein plus oil content in combination with high yield and an agronomically elite background. The variety was derived from an original cross of SN30003 and FPG2975 made at Ames, Iowa in 1998. The variety was developed as follows: F1 and F2 seed were grown at Isabela, PR in the fall of 1998 and late winter of 1999. F2 plants were selected and threshed individually. F2:3 seed was planted in a PROW (Progeny Row) plot in 1999 at Ames, Iowa. The F3 plants were selected and threshed individually from PROW plots exhibiting the best agronomic characteristics. The seed from each F3 plant was analyzed for protein content. The F3:4 lines with the highest protein content were planted in PROW plots at Ames, Iowa in 2000.

In the fall of 2000, lines with the best agronomic characteristics were harvested in bulk. Of these, the lines with the highest grain protein levels were selected for 2001 yield testing. F3:5 seed was planted at 5 locations in Iowa to test for yield and agronomic performance. Breeder seed increase will be grown in 2002 at Beaman, Iowa. Some of the criteria used to select the variety 0137472 in various generations included: yield, lodging resistance, emergence, seedling vigor, disease tolerance, maturity, plant height, seed oil and protein content.

The results of an objective description of the variety are presented below, in Table 18. Those of skill in the art will recognize that these are typical values that may vary due to environment and that other values that are substantially equivalent are within the scope of the invention.

TABLE 18

Phenotypic Description of Variety 0137472

| Trait | Phenotype |
|---|---|
| Relative Maturity | 2.4 |
| Roundup Ready | RR |
| STS | Susc. |
| Liberty | Susc. |
| Flower | Purple |
| Pubescence | Gray |
| Hilum | Imperfect Black |
| Seed Luster | |
| Seed Shape | Spherical Flattened |
| Leaf Shape | Ovate |
| Leaflet Size | Medium |
| Leaf Color | Medium Green |
| Canopy | |
| Growth Habit | Indeterminate |
| Phytophthora Allele | |
| SCN Race 3 | Susc. |
| SCN Race 14 | Susc. |
| Root Knot Nematode | Susc. |

The performance characteristics of soybean variety 0137472 were analyzed and comparisons were made with competing varieties. Characteristics examined included maturity, plant height, lodging and seed protein and oil content. The results of the analysis are presented below, in Tables 19–20.

TABLE 19

Yield Testing for Variety 0137472

| Gen. | Year | Test-Entry | # locs | Rank | # Entries |
|---|---|---|---|---|---|
| F$_{3:5}$ | 2001 | 01AHHA-8 | 5 | 20 | 50 |

TABLE 20

Performance Comparison Of Variety 0137472 Versus Competing Varieties Over 5 Locations

| Variety | YLD | % OIL | % PRO | MAT DATE | LDG | PLT HGT | FLD EMR | PHO SCR |
|---|---|---|---|---|---|---|---|---|
| 0137472 | 44.5 | 20.7 | 44.9 | 24.8 | 3.5 | 40.0 | 5.0 | 3.8 |
| DKB23-51 | 53.8 | 21.7 | 39.9 | 24.0 | 2.5 | 37.0 | 2.0 | 3.5 |
| AG2103 | 52.2 | 21.8 | 40.3 | 21.6 | 2.0 | 36.0 | 3.0 | 2.5 |
| CX198RR | 47.6 | 21.5 | 40.4 | 21.0 | 2.0 | 36.0 | 3.0 | 3.3 |
| AG1901 | 41.9 | 24.4 | 37.8 | 19.0 | 3.5 | 46.0 | 3.0 | 4.3 |
| ENTRY MEAN | 43.5 | 21.4 | 42.4 | 22.6 | 2.8 | 36.3 | 4.1 | 3.5 |
| LSD (.30) | 2.5 | 0.3 | 0.5 | 1.0 | 0.6 | 0.6 | 0.7 | 0.7 |
| LSD (.05) | 4.8 | 0.5 | 0.9 | 2.0 | 1.1 | 1.0 | 1.4 | 1.3 |
| # of TESTS | 5.0 | 5.0 | 5.0 | 5.0 | 3.0 | 3.0 | 3.0 | 4.0 |

Example 5

Development of Soybean Variety 0137441

Soybean variety 0137441 is a glyphosate resistant variety exhibiting high seed protein and protein plus oil in combination with high yield and an agronomically elite background. Soybean variety 0137441 is well adapted to the growing region of Iowa, mid-Illinois & mid-Indiana and has a maturity of 26. The variety was produced from an original cross of the soybean varieties SN30003 and AG3302 made at Ames, Iowa in 1998. The variety was developed as follows: F1 and F2 seed were grown at Isabela, PR in the fall of 1998 and late winter of 1999. F2 plants were selected and threshed individually. F2:3 seed was planted in a PROW (Progeny Row) plot in 1999 at Ames, Iowa. The F3 plants were selected and threshed individually from PROW plots exhibiting the best agronomic characteristics. The seed from each F3 plant was analyzed for protein content. The F3:4 lines with the highest protein content were planted in PROW plots at Ames, Iowa in 2000. In the fall of 2000, lines with the best agronomic characteristics were harvested in bulk. Of these, the lines with the highest grain protein levels were selected for 2001 yield testing. F3:5 seed was planted at 5 locations in Iowa to test for yield and agronomic performance. Breeder seed increase will be grown in 2002 at Beaman, Iowa. Some of the criteria used to select variety 0137441 in various generations included: yield, lodging resistance, emergence, seedling vigor, disease tolerance, maturity, plant height, seed oil and protein content.

The results of an objective description of the variety are presented below, in Table 21. Those of skill in the art will recognize that these are typical values that may vary due to environment and that other values that are substantially equivalent are within the scope of the invention.

TABLE 21

Phenotypic Description of Variety 0137441

| Trait | Phenotype |
|---|---|
| Relative Maturity | 2.6 |
| Roundup Ready | RR |
| STS | |
| Liberty | Susc. |
| Flower | Purple |
| Pubescence | Gray |
| Hilum | Imperfect Black |
| Pod Color | |
| Seed Luster | |

TABLE 21-continued

Phenotypic Description of Variety 0137441

| Trait | Phenotype |
|---|---|
| Hypocotyl Color | |
| Seed Shape | Spherical Flattened |
| Leaf Shape | Ovate |
| Leaflet Size | Medium |
| Leaf Color | Medium Green |
| Canopy | |
| Growth Habit | Indeterminate |
| Phytophthora Allele | |
| SCN Race 3 | Susc. |
| SCN Race 14 | Susc. |
| Root Knot Nematode | Susc. |

The performance characteristics of soybean variety 0137441 were analyzed and comparisons were made with competing varieties. Characteristics examined included maturity, plant height, lodging, and seed protein and oil content. The results of the analysis are presented below, in Tables 22–24.

TABLE 22

Yield Testing for Variety 0137441

| Gen. | Year | Test-Entry | # locs | Rank | # Entries |
|---|---|---|---|---|---|
| F$_{3:5}$ | 2001 | 01AHJA-35 | 5 | 24 | 50 |

TABLE 23

Exemplary Agronomic Traits of Variety 0137441 and Selected Varieties

AGRONOMIC CHARACTERISTICS

| Lines | Mat Date | Ht | Lodg | Protein | Oil | Seed/lb |
|---|---|---|---|---|---|---|
| 0137441 | 26 | | 3.0 | 45.4 | 20.4 | |
| AG2703 | 27 | | 3.0 | 39.8 | 22.1 | |
| AG2402 | 24 | | 3.5 | 40.0 | 22.5 | |

TABLE 24

Performance Comparison Of Variety 0137441 Versus Competing Varieties Over 5 Locations

| VARIETY | YLD | % OIL | % PRO | MAT DATE | LDG | FLD EMR | PHO SCR |
|---|---|---|---|---|---|---|---|
| 0137441 | 45.2 | 20.4 | 45.4 | 26.0 | 3.0 | 3.0 | 3.5 |
| DEKALB DKB31-51 | 54.0 | 22.1 | 40.4 | 32.2 | 3.0 | 3.0 | 2.5 |
| ASGROW AG2703 | 52.0 | 22.1 | 39.8 | 27.0 | 3.0 | 3.0 | 2.5 |
| DEKALB DKB28-51 | 51.7 | 21.1 | 39.8 | 29.0 | 3.5 | 1.0 | 4.0 |
| ASGROW AG3201 | 48.8 | 21.1 | 40.2 | 32.7 | 3.5 | 2.0 | 3.0 |
| DEKALB DKB26-51 | 48.3 | 22.3 | 39.4 | 25.7 | 2.5 | 2.0 | 2.5 |
| ASGROW AG2501 | 46.8 | 22.9 | 39.9 | 24.5 | 2.5 | 2.0 | 3.0 |
| DEKALB DK232-51 | 46.8 | 21.4 | 41.3 | 32.7 | 3.0 | 3.0 | 4.0 |
| ASGROW AG2402 | 46.6 | 22.5 | 40.0 | 23.5 | 3.5 | 3.0 | 3.5 |
| ASGROW AG2601 | 44.7 | 22.0 | 41.1 | 26.0 | 3.0 | 3.0 | 3.0 |
| ENTRY MEAN | 45.1 | 21.0 | 42.4 | 28.5 | 3.1 | 2.6 | 3.6 |
| LSD (.30) | 2.7 | 0.2 | 0.4 | 1.2 | 0.6 | 0.5 | 1.0 |
| LSD (.05) | 5.2 | 0.4 | 0.8 | 2.2 | 1.2 | 1.1 | 1.9 |
| # of TESTS | 5.0 | 5.0 | 5.0 | 4.0 | 2.0 | 2.0 | 2.0 |

Example 6

Development of Soybean Variety 0137810

Soybean variety 0137810 is adapted to the S. Iowa, mid-Illinois & mid-Indiana growing regions and has a maturity of 31. The variety exhibits high seed protein and protein plus oil in combination with high yield and an agronomically elite background. The variety is glyphosate resistant. The variety was derived from an original cross of soybean varieties SN30017 and AG3003 made at Ames, Iowa in 1998. The variety was developed as follows: F1 and F2 seed were grown at Isabela, PR in the fall of 1998 and late winter of 1999. F2 plants were selected and threshed individually. F2:3 seed was planted in a PROW (Progeny Row) plot in 1999 at Ames, IA. The F3 plants were selected and threshed individually from PROW plots exhibiting the best agronomic characteristics. The seed from each F3 plant was analyzed for protein content. The F3:4 lines with the highest protein content were planted in PROW plots at Ames, Iowa in 2000.

In the fall of 2000, lines with the best agronomic characteristics were harvested in bulk. Of these, the lines with the highest grain protein levels were selected for 2001 yield testing. F3:5 seed was planted at 5 locations in Iowa to test for yield and agronomic performance. Breeder seed increase will be grown in 2002 at Beaman, Iowa. The results of an objective description of the variety are presented below, in Table 25. Those of skill in the art will recognize that these are typical values that may vary due to environment and that other values that are substantially equivalent are within the scope of the invention.

TABLE 25

Phenotypic Description of Variety 0137810

| Trait | Phenotype |
|---|---|
| Relative Maturity | 3.1 |
| Roundup Ready | RR |
| STS | Susc. |
| Liberty | Susc. |
| Flower | Purple |
| Pubescence | Tawny |
| Hilum | Black |
| Pod Color | |

TABLE 25-continued

Phenotypic Description of Variety 0137810

| Trait | Phenotype |
|---|---|
| Seed Luster | |
| Hypocotyl Color | |
| Seed Shape | Spherical Flattened |
| Leaf Shape | Ovate |
| Leaflet Size | Medium |
| Leaf Color | Medium Green |
| Canopy | Intermediate |
| Growth Habit | Indeterminate |
| Phytophthora Allele | Susc. |
| SCN Race 3 | Susc. |
| SCN Race 14 | Susc. |
| Root Knot Nematode | Susc. |

The performance characteristics of soybean variety 0137810 were analyzed and comparisons were made with competing varieties. Characteristics examined included maturity, plant height, lodging, and seed protein and oil content. The results of the analysis are presented below, in Tables 26–28.

TABLE 26

Exemplary Agronomic Traits of Variety 0137810 and Selected Varieties

| | AGRONOMIC CHARACTERISTICS | | | | | |
|---|---|---|---|---|---|---|
| Lines | Mat Date | Ht | Lodg | Protein | Oil | Seed/lb |
| 0137810 | 30 | | 3.5 | 44.3 | 20.2 | |
| AG2703 | 27 | | 3.0 | 39.8 | 22.1 | |
| DKB28-51 | 29 | | 3.5 | 39.8 | 21.1 | |

TABLE 27

Yield Testing for Variety 0137810

| Gen. | Year | Test-Entry | # locs | Rank | # Entries |
|---|---|---|---|---|---|
| $F_{3:5}$ | 2001 | 01AHJA-19 | 5 | 8 | 50 |

TABLE 28

Performance Comparison Of Variety 0137810 Versus Competing Varieties Over 5 Locations

| VARIETY | YLD | % OIL | % PRO | MAT DATE | LDG | FLD EMR | PHO SCR |
|---|---|---|---|---|---|---|---|
| DEKALB DKB31-51 | 54.0 | 22.1 | 40.4 | 32.2 | 3.0 | 3.0 | 2.5 |
| ASGROW AG2703 | 52.0 | 22.1 | 39.8 | 27.0 | 3.0 | 3.0 | 2.5 |
| DEKALD DKB28-51 | 51.7 | 21.1 | 39.8 | 29.0 | 3.5 | 1.0 | 4.0 |
| ASGROW AG3201 | 48.8 | 21.1 | 40.2 | 32.7 | 3.5 | 2.0 | 3.0 |
| DEKALB DKB26-51 | 48.3 | 22.3 | 39.4 | 25.7 | 2.5 | 2.0 | 2.5 |
| Invention 0137810 | 47.8 | 20.2 | 44.3 | 30.2 | 3.5 | 2.0 | 3.5 |
| ASGROW AG2501 | 46.8 | 22.9 | 39.9 | 24.5 | 2.5 | 2.0 | 3.0 |
| DEKALB DKB32-51 | 46.8 | 21.4 | 41.3 | 32.7 | 3.0 | 3.0 | 4.0 |
| ASGROW AG2402 | 46.6 | 22.5 | 40.0 | 23.5 | 3.5 | 3.0 | 3.5 |
| ASGROW AG2601 | 44.7 | 22.0 | 41.1 | 26.0 | 3.0 | 3.0 | 3.0 |
| ENTRY MEAN | 45.1 | 21.0 | 42.4 | 28.5 | 3.1 | 2.6 | 3.6 |
| LSD (.30) | 0.2 | 0.4 | 1.2 | 0.6 | 0.3 | 1.0 | 0.9 |
| LSD (.05) | 0.4 | 0.8 | 2.2 | 1.2 | 0.8 | 1.9 | 1.3 |
| CV | 1.5 | 1.4 | 5.5 | 16.0 | 2.3 | 18.9 | 9.3 |
| # Of TESTS | 5.0 | 5.0 | 4.0 | 3.0 | 3.0 | 3.0 | 3.0 |

REFERENCES

The following references, to the extent that they provide exemplary procedural or other details supplementary to those set forth herein, are specifically incorporated herein by reference.

Allard, "Principles of Plant Breeding," John Wiley & Sons, NY, U. of CA, Davis, Calif., 50–98, 1960.

Anderson, "Weed Science Principles," West Publishing Company, 1983.

Bates, "Genetic transformation of plants by protoplast electroporation," *Mol. Biotechnol.,* 2(2):135–145, 1994.

Bernard and Weiss, "Qualitative genetics," In: *Soybeans: Improvement, Production, and Uses*, Caldwell (Ed.), *Am. Soc. of Agron.,* 117–154, 1973.

Bernard and Cremeens, "Registration of Williams '82 Soybean" *Crop Sci.,* 28:1027–1028, 1988.

Boerma and Moradshahi, "Pollen movement within and between rows to male-sterile soybeans," *Crop Sci.,* 15:858–861, 1975.

Borthwick and Parker, "Photoperiodic perception in Biloxi soybeans," *Bot. Gaz.,* 100:374–387, 1938.

Bowers, Paschall, Bernard, Goodman, "Inheritance of resistance to soybean mosaic virus in 'Buffalo' and HLS soybean" *Crop Sci.,* 32(1)67–72, 1992.

Brim and Stuber, "Application of genetic male sterility to recurrent selection schemes in soybeans," *Crop Sci.,* 13:528–530, 1973.

Burton, "Breeding soybeans for improved protein quantity and quality," In *Proc. Of the World Soybean Res.,* Shibles (ed). Conf. III, Ames, I A, Westview Press, Inc. Boulder, Colo., 361–367, 1984.

Burton, "Quantitative genetics: results relevant to soybean breeding," In: Soybeans: *Improvement, Production, and Uses*. Wilcox (ed), Am. Soc. Agron., Madison, Wis., 211–248, 1987.

Byth, Weber, and Caldwell, "Correlated truncation selection for yield in soybeans," *Crop Sci.,* 6:249–251, 1969.

Caldwell, Weber, Byth, "Selection value of phenotypic attributes in soybeans," *Crop Sci.,* 6:249–251, 1966.

Carlson, "Morphology", In: *Soybeans: Improvement, Production, and Uses*, Caldwell (Ed.), Am. Soc. Agron., Madison, Wis., 17–95, 1973.

Chee and Slightom, "Transformation of soybean (*Glycine max*) via *Agrobacterium tumefaciens* and analysis of transformed plants," *Methods Mol. Biol.,* 44:101–119, 1995.

Christianson, Warnick, Carlson, "A morphogenetically competent soybean suspension culture," *Science,* 222:632–634, 1983.

Cianzio and Fehr, "Genetic variability for soybean seed composition in crosses between high and low protein parents," *J. Agric. Univ. PR,* 66:123–129, 1982.

Criswell and Hume, "Variation in sensitivity to photoperiod among early maturing soybean strains," *Crop Sci.,* 12:657–660, 1972.

Dhir, Dhir Sturtevant, Winholm, "Regeneration of transformed shoots for electroporated soybean *Glycine max* L. Merr. protoplasts," *Plant Cell Rep.,* 10(2):97–101, 1991.

Fehr, "Soybean," *In: Hybridization of Crop Plants*, Fehr and Hadley (Eds.), Am. Soc. Agron. and Crop Sci. Soc. Am., Madison, Wis., 90–599, 1980.

Fehr, *In: Soybeans: Improvement, Production and Uses,* 2nd Edition, *Manograph.,* 16:249, 1987a.

Fehr, "Principles of variety development," *Theory and Technique*, (Vol 1) and *Crop Species Soybean* (Vol 2), Iowa State Univ., Macmillian Pub. Co., NY, 360–376, 1987b.

Finer, Cheng, Verma, "Soybean transformation: Technologies and progress," *In: Soybean: Genetics, Molecular Biology and Biotechnology*, CAB Intl., Verma and Shoemaker (ed), Wallingford, Oxon, UK, 250–251, 1996.

Fraley, Rogers, Horsch, Eichholtz, Flick, Fink, Hoffmann, Sanders, "The sev system a new disarmed ti plasmid vector system for plant transformation," *Bio. Tech.,* 3(7): 629–635, 1985.

Fromm, Taylor, Walbot, "Stable transformation of maize after gene transfer by electroporation," *Nature,* 319(6056):791–793., 1986.

Fulmer, "The soybean as a chemical factory. In: *Soybean Utilization Alternatives*, McCann (ed), The Center for Alternative Crops and Products, Univ. of Minnesota, 1–12, 1988.

Hamner, "*Glycine max*(L.) Merrill," *In: The Induction of Flowering: Some Case Histories*, Evans (ed), Cornell Univ. Press, Ithaca, N.Y., 62–89, 1969.

Hartweck, Lazzeri, Cui, Collins, Williams "Auxin orientation effects on somatic embryogenesis from immature soybean cotyledons," *In Vitro Cell. Develop. Bio.,* 24:821–828, 1988.

Hartwig, "Breeding soybeans for high protein content and quality," In: *New approaches to breeding for improved plant protein*, Intl. Atomic Energy Agency, Vienna, 67–70, 1969.

Hartwig, "Varietal improvement," In: *Soybeans: Improvement, production, and uses*, Caldwell (ed) 1st ed., Agronomy, 16:187–210, 1969.

Hartwig, "Breeding productive soybeans with a higher percentage of protein. In: *Seed protein improvement in cereals and legumes*, Vol. II, Intl. Atomic Energy Agency, Vienna, 59–66, 1979.

Hinson et al., "Associations between chemical composition of seed and seed yield of soybeans," *Crop Sci.,* 22:829–830, 1972.

Hymowitz, "Soybeans," In: *Evolution in crop plants*, Simmonds (ed) Longman Group, London, 159–162, 1976.

Johnson and Bernard, "Soybean genetics and breeding," In: *The Soybean*, Norman (ed), Academic Press, NY, 1–73, 1963.

Johnson, "Breeding for oil and protein in soybeans," *Soybean Dig.,* 21(11):73–75, 1961.

Kiihl, Hartwig, Kilen, "Grafting as a tool in soybean breeding," *Crop Sci.,* 17:181–182, 1977.

Klee, Yanofsky, Nester, "Vectors for transformation of higher plants," *Bio. Tech.,* 3(7):637–642, 1985.

Kuehl, "Pollen viability and stigma receptivity of *Glycine max* (L.) Merrill," Thesis, North Carolina State College, Raleigh, N.C., 1961.

Kwon and Torrie, "Heritability of and interrelationships among traits of two soybean populations," *Crop Sci.,* 4:196–198, 1964.

Lazzeri, "Stable transformation of barley via direct DNA uptake. Electroporation- and PEG-mediated protoplast transformation," *Methods Mol. Biol.,* 49:95–106, 1995.

Leffel, "High protein lines and chemical constituent pricing in soybean," *J. Prod. Agric.,* 1:111–115, 1988.

Leffel and Rhodes, "Agronomic performance and economic value of high-seed-protein soybean," *J. Prod. Agric.,* 6:365–368, 1993.

Major, Johnson, Tanner, Anderson, "Effects of daylength and temperature on soybean development," *Crop Sci.,* 15:174–179, 1975.

Marcotte and Bayley, Quatrano, "Regulation of a wheat promoter by abscisic acid in rice protoplasts," *Nature,* 335(6189):454–457, 1988.

Mounts, Wolf, Martinez, "Processing and utilization," In: *Soybeans: Improvement, Production, and Uses*, Wilcox (ed), *Am. Soc. Agron.*, Madison, Wis., 1987.

Nickell and Bernard, "Registration of L84–5873 and L84–5932 soybean germplasm lines resistant to brown stem rot," *Crop Sci.,* 32(3):835, 1992.

Omirulleh, Abraham, Golovkin, Stefanov, Karabaev, Mustardy, Morocz, Dudits, "Activity of a chimeric promoter with the doubled CaMV 35S enhancer element in protoplast-derived cells and transgenic plants in maize," *Plant Mol. Biol.,* 21(3):415–428, 1993.

Openshaw and Hadley, "Selection indices to modify protein concentration of soybean seeds," *Crop Sci.,* 24:1–4, 1984.

Orf, "Modifying soybean composition by plant breeding," In: *Soybean utilization alternative*, Univ. Minnesota Center Alternative Crops and Products, McCann (ed), St. Paul, 131–141, 1988.

Pantalone, Burton, Carter, Jr., "Soybean fibrous root heritability and genotypic correlations with agronomic and seed quality characteristics," *Crop Sci.,* 36:1120–1125, 1996.

Parker, Hendricks, Borthwick, Scully, "Action spectrum for the photoperiodic control of floral initiation of short-day plants," *Bot. Gaz.,* 108:1–26, 1946.

Poehlman and Sleper, "Breeding Field Crops" Iowa State University Press, Ames, 1995.

Potrykus, Paszkowski, Saul, Petruska, Shillito, "Molecular and general genetics of a hybrid foreign gene introduced into tobacco by direct gene transfer," *Mol. Gen. Genet.,* 199(2):169–177, 1985.

Sebern and Lambert, "Effect of stratification for percent protein in two soybean populations," *Crop Sci.,* 24:225–228, 1984.

Serretti, Schapaugh, Jr., Leffel, "Amino acid profiles of high seed protein soybean," *Crop Sci.,* 34:207–209, 1994.

Shanmugasundaram and Tsou, "Photoperiod and critical duration for flower induction in soybean," *Crop Sci.,* 18:598–601, 1978.

Shannon, Wilcox, Probst, "Estimated gains from selection for protein and yield in the F4 generation of six soybean populations," *Crop Sci.,* 12:824–826, 1972.

Shibles, Anderson, Gibson, "Soybean," In: *Crop Physiology, Some Case Histories*, Evans (ed), Cambridge Univ. Press, Cambridge, England, 51–189, 1975.

Simmonds, "Principles of crop improvement," Longman, Inc., NY, 369–399, 1979.

Simpson, Jr. and Wilcox, "Genetic and phenotypic associations of agronomic characteristics in four high protein soybean populations," *Crop Sci.,* 23:1077–1081, 1983.

Sneep and Hendriksen, "Plant breeding perspectives," Wageningen (ed), Center for Agricultural Publishing and Documentation, 1979.

Sprague and Dudley, *Corn and Improvement,* 3rd ed., 1988.

Thorne and "Incorporation of high protein, exotic germplasm into soybean populations by 2- and 3-way crosses," *Crop Sci.,* 10:652–655, 1970.

Uchimiya, Fushimi, Hashimoto, Harada, Syono, Sugawara, "Expression of a foreign gene in callus derived from DNA-treated protoplasts of rice (*Oryza-sativa*)" *Mol. Gen. Genet.,* 204(2):204–207, 1986.

van Schaik and Probst, "Effects of some environmental factors on flower production and reproductive efficiency in soybeans," *Agron. J.,* 50:192–197, 1958.

Walker, Cianzio, Bravo, Fehr, "Comparison of emasculation and nonemasculation for artificial hybridization of soybeans," *Crop Sci.,* 19:285–286, 1979.

Wang et al., "Large-scale identification, mapping, and genotyping of single-nucleotide polymorphisms in the human genome," *Science,* 280:1077–1082, 1998.

Wehrmann, Fehr, Cianzio, Cavins, "Transfer of high seed protein to high-yielding soybean cultivars," *Crop Sci.,* 27:927–931, 1987.

Wilcox and Cavins, "Backcrossing high seed protein to a soybean cultivar," *Crop Sci.,* 35:1036–1041, 1995.

Williams et al., "Oligonucleotide primers of arbitrary sequence amplify DNA polymorphisms which are useful as genetic markers," *Nucleic Acids Res.,* 18:6531–6535, 1990.

Wright, Koehler, Hinchee, Carnes, "Plant regeneration by organogenesis in *Glycine max*," *Plant Cell Reports,* 5:150–154, 1986.

What is claimed is:

1. A seed of soybean variety 0137335, wherein a sample of said seed has been deposited under ATCC Accession No. PTA-8110.

2. A plant produced by growing the seed of claim 1.

3. A plant part of the plant of claim 2.

4. The plant part of claim 3, further defined as pollen, an ovule or a cell.

5. A soybean plant having all of the physiological and morphological characteristics of the plant of claim 2.

6. A tissue culture of regenerable cells of soybean variety 0137335, wherein the tissue culture regenerates soybean plants capable of expressing all the physiological and morphological characteristics of the soybean variety 0137335 and wherein a sample of the seed of said soybean variety 0137335 has been deposited under ATCC Accession No. PTA-8110.

7. The tissue culture of claim 6, wherein the regenerable cells are embryos, meristematic cells, pollen, leaves, roots, root tips or flowers or are protoplasts or callus derived therefrom.

8. A soybean plant regenerated from the tissue culture of claim 6, wherein the regenerated soybean plant is capable of expressing all the physiological and morphological characteristics of the soybean variety 0137335, and wherein a sample of the seed of said soybean variety 0137335 has been deposited under ATCC Accession No. PTA-8110.

9. The soybean plant of claim 2, further comprising a single locus conversion.

10. The soybean plant of claim 9, wherein the single locus conversion comprises a dominant allele.

11. The soybean plant of claim 9, wherein the single locus conversion comprises a recessive allele.

12. The soybean plant of claim 9, wherein the single locus was stably inserted into a soybean genome by transformation.

13. The soybean plant of claim 9, wherein said single locus comprises a single gene.

14. A first generation ($F_1$) hybrid soybean seed having a male parent and a female parent, wherein the male and female parents each comprise a diploid genome having a plurality of paired chromosomes comprising a plurality of mappable genetic loci with a pair of alleles at each locus, each parent further being homozygous with respect to each allele pair;
the hybrid soybean seed also comprising a diploid genome having a plurality of paired chromosomes comprising a plurality of mappable genetic loci with a pair of alleles at each locus, one of the alleles being contributed by the male parent and the other being contributed by the female parent, wherein one of the parents is a plant of soybean variety 0137335, a sample of the seed of said soybean variety 0137335 having been deposited under ATCC Accession No. PTA-8110, and wherein the other parent is a plant of a different variety;
whereby one allele at each locus in the hybrid genome is found at the same locus in soybean avariety 0137335, and further whereby the other allele is found at the same locus in the other parent.

15. A first generation $F_1$ hybrid soybean plant produced by growing the seed of claim 14.

16. A method of producing soybean seed, comprising crossing a plant of soybean variety 0137335 with itself or a second soybean plant, wherein a sample of the seed of said soybean variety 0137335 has been deposited under ATCC Accession No. PTA-8110.

17. The method of claim 16, further defined as a method of preparing $F_1$ hybrid soybean seed, comprising crossing a plant of soybean variety 0137335 to a second, different soybean plant, wherein a sample of the seed of said soybean variety 0137335 has been deposited under ATCC Accession No. PTA-8110.

18. The method of claim 17, further defined as a method of preparing $F_2$ hybrid soybean seed and further comprising the steps of:
(a) growing the $F_1$ hybrid soybean seed to produce an $F_1$ hybrid soybean plant; and
(b) crossing the $F_1$ hybrid soybean plant with itself or a different soybean plant to produce $F_2$ hybrid soybean seed.

19. The method of claim 18, further defined as a method of preparing $F_3$ hybrid soybean seed and further comprising the steps of:
(c) growing the $F_2$ hybrid soybean seed to produce an $F_2$ hybrid soybean plant; and
(d) crossing the $F_2$ hybrid soybean plant with itself or a different soybean plant to produce $F_3$ hybrid soybean seed.

20. The method of claim 17, wherein crossing comprises the steps of:
(a) planting a seed of soybean variety 0137335 and a second, distinct soybean plant, wherein a sample of the seed of said soybean variety 0137335 has been deposited under ATCC Accession No. PTA-8110;
(b) growing soybean plants from said seed until said plants bear flowers;
(c) cross pollinating a flower of said soybean variety 0137335 with pollen from said second soybean plant or cross pollinating a flower of said second soybean plant with pollen from said soybean variety 0137335; and
(d) harvesting seed resulting from said cross pollinating.

21. A method for developing a soybean plant in a soybean breeding program comprising:
(a) obtaining the soybean plant, or its parts, of claim 2; and
(b) employing said plant or parts as a source of breeding material using plant breeding techniques.

22. The method of claim 21, wherein the plant breeding techniques are selected from the group consisting of recurrent selection, mass selection, bulk selection, backcrossing, pedigree breeding, genetic marker-assisted selection and genetic transformation.

23. A method of producing a soybean plant derived from the soybean variety 0137335, the method comprising the steps of:
(a) preparing a progeny plant derived from soybean variety 0137335 by crossing a plant of the soybean variety 0137335 with a second soybean plant, wherein a sample of the seed of the soybean variety 0137335 was deposited under ATCC Accession No. PTA-8110; and
(b) crossing the progeny plant with itself or a second plant to produce a progeny plant of a subsequent generation which is derived from a plant of the soybean variety 0137335.

24. The method of claim 23, further comprising:
(c) crossing the progeny plant of a subsequent generation with itself or a second plant; and
(d) repeating steps (b) and (c) for at least 2–10 additional generations to produce a soybean plant derived from the soybean variety 0137335.

25. The method of claim 24, further comprising:

(a) crossing said soybean variety 0137335-derived soybean plant with itself or another soybean plant to yield additional soybean variety 0137335-derived progeny soybean seed;

(b) growing said progeny soybean seed of step (a) under plant growth conditions, to yield additional soybean variety 0137335-derived soybean plants; and (c) repeating the crossing and growing steps of (a) and (b) from 0 to 7 times to generate further soybean variety 0137335-derived soybean plants.

26. A method for producing a single locus converted plant of soybean variety 0137335, the method comprising the steps of:

(a) crossing a plant of soybean variety 0137335 with a second soybean plant comprising a single locus to produce a progeny plant comprising the single locus;

(b) backcrossing the progeny plant with a plant of soybean variety 0137335 to produce a backcrossed progeny plant comprising the single locus; and (c) repeating the backcrossing of step (b) over a number of generations sufficient to obtain a single locus converted plant of soybean variety 0137335.

* * * * *